US009085536B2

(12) United States Patent
Du Bois et al.

(10) Patent No.: US 9,085,536 B2
(45) Date of Patent: Jul. 21, 2015

(54) ACONITINE COMPOUNDS, COMPOSITIONS, USES, AND PREPARATION THEREOF

(75) Inventors: Justin Du Bois, Menlo Park, CA (US); Brian M. Andresen, Sharon, MA (US); Frederic Menard, Kelowna (CA); Andrew W. Patterson, Somerville, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 346 days.

(21) Appl. No.: 13/421,809

(22) Filed: Mar. 15, 2012

(65) Prior Publication Data

US 2012/0238526 A1 Sep. 20, 2012

Related U.S. Application Data

(60) Provisional application No. 61/453,105, filed on Mar. 15, 2011.

(51) Int. Cl.
*A61K 31/439* (2006.01)
*C07D 221/22* (2006.01)

(52) U.S. Cl.
CPC .................................... *C07D 221/22* (2013.01)

(58) Field of Classification Search
USPC ............................................ 514/279; 546/39
See application file for complete search history.

(56) References Cited

U.S. PATENT DOCUMENTS

| | | | |
|---|---|---|---|
| 5,478,833 | A | 12/1995 | Murayama et al. |
| 5,478,834 | A | 12/1995 | Murayama et al. |
| 5,496,825 | A | 3/1996 | Murayama et al. |
| 5,514,684 | A | 5/1996 | Murayama et al. |
| 5,770,604 | A | 6/1998 | Murayama |

FOREIGN PATENT DOCUMENTS

| | | | |
|---|---|---|---|
| EP | 739882 | A1 | 10/1996 |
| EP | 1790341 | A1 | 5/2007 |

OTHER PUBLICATIONS

Liu, M. et al.: LC separation and determination of five diester-diterpenoid alkaloids in the unprocessed and processed acotine roots. Chromatographia, vol. 67, pp. 1003-1006, 2008.*
Korean Intellectual Property Office, "Written Opinion of the International Searching Authority" in PCT International Application No. PCT/US2012/029302, Sep. 12, 2012.
Wiesner et al., "A rigorous, purely chemical structure proof for aconitine and delphinine", Canadian J. Chem. 47:2734 (1969).
Wang et al., "Voltage-gated sodium channels as primary targets of diverse lipid-soluble neurotoxins", Cellular Signalling 15:151 (2003).
Borcsa et al., "Semisynthesis and pharmacological investigation of lipo-alkaloids prepared from aconitine", Fitoterapia 82:365 (2011).
Pelletier, "Studies in the chemistry of natural products: rearrangement reactions of diterpenoid and norditerpenoid alkaloids", Journal of Natural Products 55:1 (1992).
Catterall et al. (2005) Pharmacol. Rev. 57:397-409.
Singhuber et al. (2009) J. Ethnopharmacol. 126:18-30.
Ameri (1998) Progress in Neurobiology 56:211-35.
Tsuchida et al. (2009) J. Urology 181(4):23-24.
Kudo et al. (2009) International Continence Society, 39th Annual Meeting, Abstract 684.

* cited by examiner

*Primary Examiner* — Charanjit Aulakh
(74) *Attorney, Agent, or Firm* — David A. Roise; VLP Law Group LLP

(57) ABSTRACT

Compound derivatives of aconitine are provided, in particular derivatives that modulate the activity of sodium channels. Also provided are pharmaceutical compositions comprising compounds of the invention and a pharmaceutically acceptable carrier. The subject compounds are useful in treatments, including treatments to modulate neuronal activity or to bring about muscular relaxation. The compounds also find use in the treatment of subjects suffering from a voltage-gated sodium channel-enhanced ailment or from pain. Further methods are provided for the preparation of the aconitine derivatives.

36 Claims, 10 Drawing Sheets

(-)-tetrodotoxin (+)-saxitoxin

ACONITINE COMPOUNDS, COMPOSITIONS, USES, AND PREPARATION THEREOF

CROSS-REFERENCE TO RELATED APPLICATION

This application claims the benefit of U.S. Provisional Application No. 61/453,105, filed on Mar. 15, 2011, the disclosure of which is incorporated herein by reference in its entirety.

BACKGROUND OF THE INVENTION

Aconitine is an alkaloid neurotoxin that is produced by various species of the genus *Aconitum*, such as wolfsbane and monkshood. Despite its toxicity, aconitine has seen a limited use as a medicine since its discovery, for example in the treatment of neuralgia, fever, pericarditis, and nervous palpitation. Calculation of an appropriate dosage is difficult, however, due to the narrow therapeutic index. Aconitine is known to open tetrodotoxin (TTX)-sensitive sodium channels in the heart and other tissues, and it has been used to create models of cardiac arrhythmia. See, for example, Wang and Wang *Cellular Signaling* 2003, 15, 151-159.

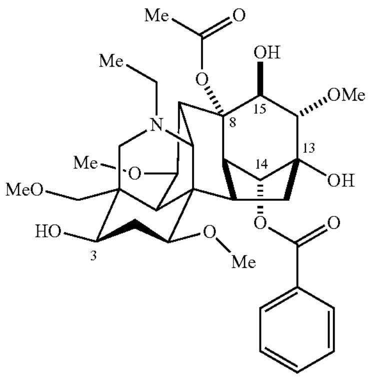

aconitine

The structure of aconitine was determined over fifty years ago (Wiesner et al. *Tetrahedron Lett.* 1959, 2, 15) and various semisynthetic modifications of the molecule have been reported. For example, U.S. Pat. No. 5,770,604 reports the modification of aconitine by hydrolysis of the C-14 benzoate moiety and subsequent acylation of the resulting C-14 hydroxyl group with various modified benzoyl groups. The initial hydrolysis step is not selective, however, and the resulting aconine compounds lack the acetyl group on the C-8 hydroxyl that is normally found in the natural product.

Likewise, U.S. Pat. Nos. 5,478,833; 5,478,834; 5,496,825; and 5,770,604 report the modification of known aconitine alkaloids, such as aconitine, mesaconitine, hypaconitine, and jesaconitine, and various aconine compounds lacking the C-8 acetyl group, by deoxygenation at positions 3, 8, 13, or 15, or by replacement of substituents at the ring nitrogen or at positions 1, 8, or 14. These reactions show limited selectivity, however, and do not allow for targeted substitution at the C-8 and C-14 positions of the natural aconitine structure.

Borcsa et al., *Fitoterapia* 2011, 82, 365-368, provide the semisynthesis and pharmacological investigation of lipo-alkaloids prepared from aconitine. According to the reported methods, the acetyl group at C-8 is transesterified with fatty acyl moieties. No modification of the C-14 benzoyl group was reported, however.

The rearrangement reactions of aconitine and other related diterpenoid and norditerpenoid alkaloids have been reviewed. See Pelletier, *J. Natural Prod.* 1992, 55, 1-24.

The strong therapeutic potential of aconitine in the treatment of pain and other diseases of the nervous system make it an attractive candidate for structural modification and analysis. There is thus a need for improved compound derivatives of aconitine, pharmaceutical compositions, methods of use, and methods of preparation.

SUMMARY OF THE INVENTION

The present invention addresses these and other problems by providing compounds, pharmaceutical compositions, methods of use of compounds, and methods of preparation of compounds relating to aconitine.

In particular, according to one aspect of the invention, compounds are provided as represented by structural formula (II):

(II)

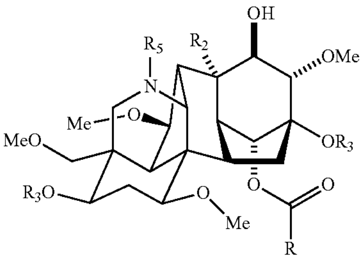

or a pharmaceutically acceptable salt or prodrug thereof, wherein:

R is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

$R_2$ is alkyl, alkoxy, or,

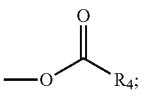

each $R_3$ is independently hydrogen or a protecting group;

each $R_4$ is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamindo, or azido; and $R_5$ is alkyl;

provided that, when R is unsubstituted phenyl, $R_2$ is

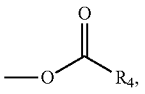

and each $R_3$ is hydrogen, then $R_4$ is not alkyl or alkenyl; and when R is p-methoxyphenyl, $R_2$ is

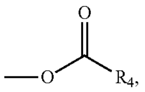

and each $R_3$ is hydrogen, then $R_4$ is not methyl.

In specific embodiments of the invention, each $R_3$ group is hydrogen.

In other specific embodiments, the $R_2$ group is

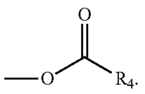

In more specific embodiments, the $R_4$ group is alkyl. In even more specific embodiments, $R_4$ is methyl.

In some embodiments, the $R_5$ group is methyl or ethyl, and in preferred embodiments, the $R_5$ group is ethyl.

According to some embodiments of the invention, R is alkyl, aryl, heteroaryl, heterocyclyl, or cycloalkyl, and is optionally substituted with 1 to 3 A groups.

In specific embodiments, R is alkyl, phenyl, naphthyl, cyclohexyl, or coumarinyl, and is optionally substituted with 1 to 3 A groups.

In other specific embodiments, the A groups are independently alkyl, alkoxyl, halo, trihalomethyl, or azido.

In preferred embodiments, R is aryl, heteroaryl, or cycloalkyl, and is optionally substituted with 1 to 3 A groups.

In specific embodiments, the R group is selected from any one of the following:

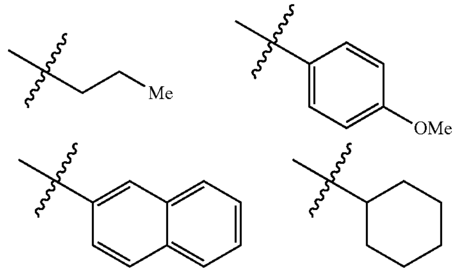

-continued

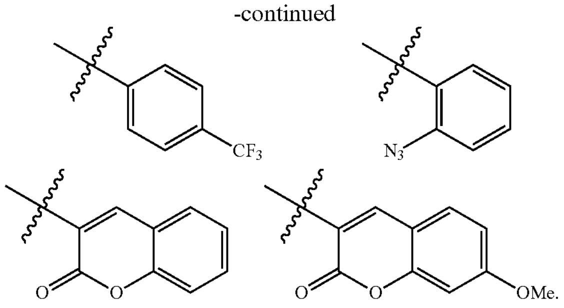

In more specific embodiments, the R group is

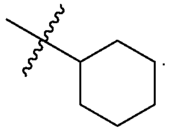 [SMILES: *C1CCCCC1]

Also provided according to the invention are compounds of structural formula (II), wherein each $R_3$ is a protecting group. In some embodiments, the protecting group is a silyl protecting group. In more specific embodiments, the protecting group is t-butyldimethylsilyl or trimethylsilyl. In even more specific embodiments, the protecting group is trimethylsilyl.

According to some embodiments of the invention, the compound of structural formula (II) modulates the activity of a sodium channel.

In some embodiments, the compound causes the sodium channel to open. In specific embodiments, the compound causes the sodium channel to open at a lower membrane potential than aconitine.

In some embodiments, the compound causes decreased flow of sodium through the sodium channel.

According to another aspect, the invention provides pharmaceutical compositions comprising the subject compound and a pharmaceutically acceptable carrier.

According to yet another aspect, the invention provides packaged pharmaceuticals comprising the subject pharmaceutical composition and instructions for using the composition to treat pain in a mammalian subject.

According to still yet another aspect, the invention provides methods of treatment in a subject, comprising administering to the subject a compound of the invention in an amount effective to treat the subject.

In one embodiment, the treatment modulates neuronal activity in the subject or brings about muscular relaxation in the subject.

In another embodiment, the subject suffers from a voltage-gated sodium channel-enhanced ailment.

In specific embodiments, the voltage-gated sodium channel-enhanced ailment is selected from the group consisting of: acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, blepharospasm, cancer, cardiac arrythmia, epilepsy, focal dystonia, hyperhidrosis, muscle spasms, and urinary bladder relaxation.

In another embodiment, the subject suffers from pain.

In specific embodiments, the pain is acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, or pain from dysmenorrhea.

In still another embodiment, the treatment reduces or eliminates wrinkles.

In specific embodiments, the subject of the treatment methods is a mammalian subject, and may be, more specifically, a human subject.

The invention also provides, in another aspect, methods of preparing an aconitine derivative, comprising the step of:

i) selectively protecting an aconitine congener at the C-3 and C-13 hydroxyl groups.

According to certain specific embodiments, the selective protection is with a silyl group.

According to more specific embodiments, the silyl group is a t-butyldimethylsilyl group or a trimethylsilyl group.

According to even more specific embodiments, the silyl group is a trimethylsilyl group.

In some embodiments of the invention, the method of preparing an aconitine derivative further comprises the step of selectively cleaving the C-14 ester of the protected aconitine congener.

In specific embodiments, the selective cleavage is a reductive cleavage.

In more specific embodiments, the reductive cleavage is by diisobutylaluminum hydride.

In some embodiments of the invention, the method of preparing an aconitine derivative further comprises the step of selectively modifying the C-14 hydroxyl group of the cleaved protected aconitine congener.

In specific embodiments, the selective modification is an acylation.

DETAILED DESCRIPTION OF THE INVENTION

Bioelectricity and the Action Potential

Figure 1:
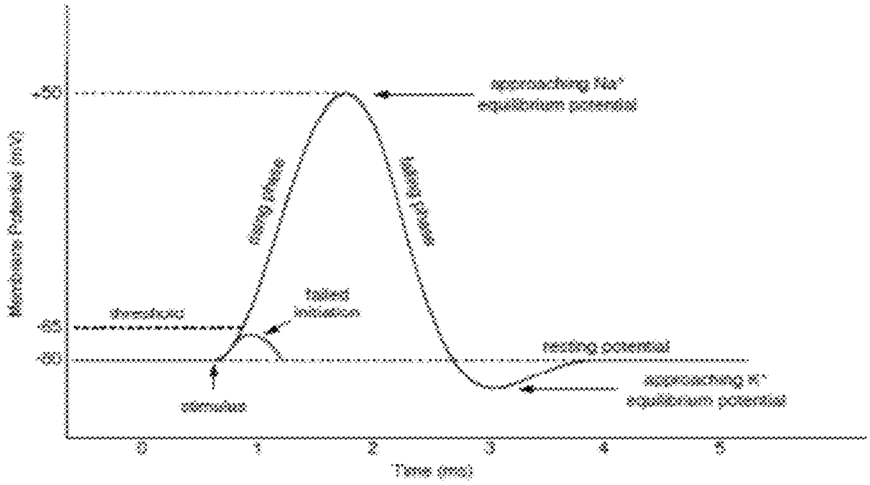
FIG. 1. The action potential as a plot of membrane potential vs. time.

The action potential is the fundamental unit of communication of excitable cells (Johnston et al., *Foundations of Cellular Neurophysiology*; The MIT Press: Cambridge, Mass., 1995). Defined as a transient reversal of membrane potential, an action potential is propagated along the length of an axon by the concomitant action of voltage-gated sodium and potassium ion channels ($Na_V$ and $K_V$, respectively). Central to their function is the development and maintenance of membrane potential (Wright, *Adv. Physiol. Educ.* 2004, 28, 139-42).

Transmembrane voltages exist for all mammalian cells and range in value from −40 to −90 mV. Membrane potential derives from the equilibration of electric potential and chemical potential across a cell membrane. The $Na^+/K^+$-ATPase, which is responsible for about 70% of energy consumption of the entire nervous system, transports three $Na^+$ ions out of the cell while pumping two $K^+$ ions into the cell per cycle, creating $Na^+$ and $K^+$ concentration gradients across the cell membrane. While cell membranes are impermeant to polar species, the membranes of excitable cells contain leak channels that are more permeant to potassium ions than to sodium ions. Therefore, potassium ions flow down their concentration gradient from inside the cell to the outside, making the outside of the cell positive relative to the inside of the cell. The resulting electric potential becomes stronger and the driving force for passage of potassium ions across the membrane becomes weaker since the developing electric potential opposes the diffusion force.

In the absence of any other leak channels, the potential at which these two forces are in equilibrium is the potassium equilibrium potential and is defined by the Nernst equation:

$$E = \frac{RT}{zF}\ln\frac{[\text{ion outside cell}]}{[\text{ion inside cell}]}$$

where E is the equilibrium potential for potassium, R is the ideal gas constant, T is temperature, z is the charge on potassium ion, and F is Faraday's constant. In a typical mammalian cell at 37° C., [$K^+$ outside cell] is 5 mM, and [$K^+$ inside cell] is 140 mM, giving a potassium equilibrium potential of −89 mV.

The sodium equilibrium potential can be similarly calculated. The sodium equilibrium potential is less important than the potassium equilibrium potential in the discussion of membrane potential because most leak channels are far less conductive to sodium ions than to potassium ions. However, the sodium equilibrium potential becomes more important over the course of an action potential, as is discussed below. Calculated in the same manner, the sodium equilibrium potential ($Na^+$ outside cell=145 mM, $Na^+$ inside cell=10 mM) is determined to be +71 mV.

Membrane potential can be more precisely determined by taking a weighted average of the potassium and sodium equilibrium potentials, with the magnitude of weighting determined by ion permeability. This method of determining membrane potential is captured in the Goldman equation:

$$V_m = E_{Na}\frac{G_{Na}}{G_{Na}+G_K} + E_K\frac{G_K}{G_{Na}+G_K}$$

where $V_m$ is membrane potential, $E_X$ is the equilibrium potential for ion X, and $G_X$ is the conductance of ion X. Using the above determined equilibrium potentials for $Na^+$ and $K^+$, and assuming $G_K$=20 $G_{Na}$ (i.e. the membrane is 20 times more permeable to potassium than to sodium at resting potential), membrane potential is found to be −81 mV, which closely correlates to experimentally determined values in mammalian neurons.

While these leak channels play a critical role in the development and maintenance of membrane potential, it is the concomitant action of voltage-gated sodium and potassium ion channels that propagate action potentials (see FIG. 1) (Hille, *Ion Channels of Excitable Membranes,* 3rd ed.; Sinauer Associates: Sunderland, Mass., 2001) These ion channels gate (i.e., open and close) in response to changes in membrane potential. Most of these channels remain closed at resting potential, however, if a sufficiently large depolarization occurs, a positive feedback response results. While both sodium and potassium channels open in response to depolarization, sodium channels open faster. Therefore, inward sodium current dominates the first phase of an action potential, swamping any currents associated with leak channels and causing further depolarization of the membrane. In this "rising phase" of an action potential, membrane potential rapidly approaches the sodium equilibrium potential as sodium ion channels represent most of the membrane's ionic conductance. Furthermore, this "all or nothing" characteristic of an action potential means that once a certain threshold potential is achieved, an action potential is "fired". The characteristics of this action potential depend not on the characteristics of the initial stimulus, but on the organization and concentration of ion channels in the neuron. In the "falling phase" of an action potential, sodium channels become inactivated and the outward current of potassium channels dominates, moving the membrane potential back towards the potassium equilibrium potential and repolarizing the membrane. This depolarization-repolarization cycle is propagated along the membranes of excitable cells, and along with the action of neurotransmitters at synapses, forms the basis of all neuronal signaling.

Structural Features of Tetrameric Ion Channels

Figure 2:
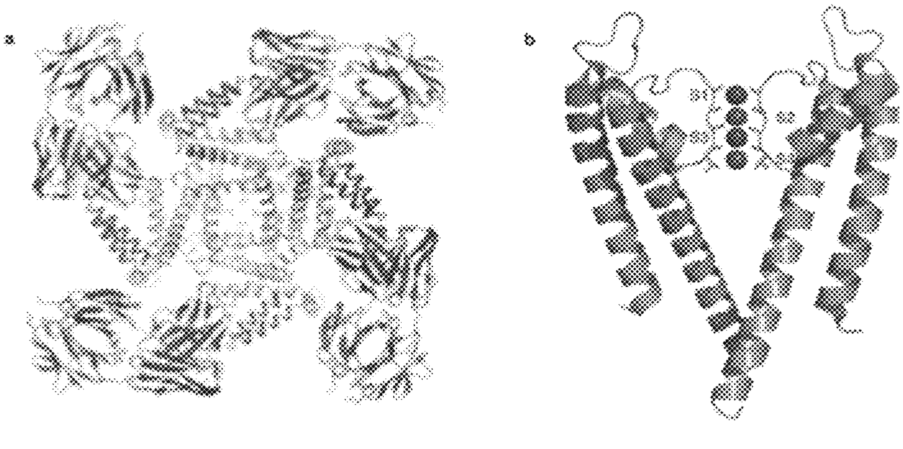
FIG. 2. Crystal structures of the potassium channel. (a) Top view of $K_V$AP, a bacterial voltage-gated potassium channel in complex with Fab (Jiang et al., *Nature* 2003, 423, 33-41). PDB 1ORQ. (b) Side view showing the selectivity filter of KcsA, a bacterial potassium channel (Zheu et al., *Nature* 2001, 414, 43-48). For clarity, only two domains are shown. $K^+$ ions (second and fourth spheres, from top) are interspersed with water molecules (first and third spheres, from top) at each of the ion binding sites (S1-S4). PDB 1K4C.

Voltage-gated ion channels are unique molecular machines that alter their conformation in response to changes in membrane potential. Because of their ubiquity in the nervous systems of all life forms, their structure and mechanics are of great interest. A large body of structural information exists for the potassium channel as X-ray crystal structures of both eukaryotic and prokaryotic proteins have been solved. A review of the general features of the potassium channel is instructive to our understanding of the features of the sodium channel. Potassium channels exist as tetrameric structures in which four protein subunits, each containing six transmembrane α-helices (S1-S6), arrange in a C-4 symmetric manner around a central, ion-conducting pore (see FIG. 2). In some cases these four proteins are identical, in others they are related but not identical. Of particular interest is the channel pore, which must discriminate between potassium ions and the smaller sodium and lithium ions. Nearly all known potassium channels contain a threonine-valine-glycine-tyrosine-glycine (T-V-G-Y-G) signature sequence in each domain, which lines the channel pore and comprises the selectivity filter (Heginbotham et al., *Science* 1992, 258, 1152-1155). Mutation of any of these residues severely compromises ion selectivity (Heginbotham et al., *Biophys. J.* 1994, 66, 1061-1067).

Selectivity for potassium over the smaller sodium ion derives from thermoneutral dehydration of potassium ions as they enter the selectivity filter (Doyle et al., *Science* 1998, 280, 69-77). The dimensions of the selectivity filter allow for precise binding and stabilization of naked potassium ions through interactions with backbone carbonyls in the signature sequence. The hydrated sodium ion is too large to fit into the selectivity filter, and the dehydrated ion is not effectively stabilized, so that dehydration is thermodynamically disfavored. The permeability of lithium ions through $K_V$ in its conductive state is immeasurably low, and selectivity for potassium over sodium is >10,000:1.

In spite of strong binding interactions within the selectivity filter for dehydrated potassium ions, conduction rates as high as $10^8$ ions/second, approaching the diffusion limit, are achieved. This high conductivity can be explained by the fact that the selectivity filter contains four $K^+$ binding sites in relatively close proximity—the total length of the selectivity filter is about 7.5 Å. When a single $K^+$ ion is bound in the selectivity filter there is a strong attractive interaction between protein and ion, however when two ions are bound, this attractive interaction is balanced by an electrostatic repulsion between the two cations. At physiologically relevant $K^+$ concentrations (150 mM), two $K^+$ ions are contained in the selectivity filter at any given time, eliminating any thermodynamic preference for a single ion to remain lodged in the channel pore (Morais-Cabral et al., *Nature* 2001, 414, 37-42).

Structure and Mechanics of the Voltage-Gated Sodium Channel

In contrast to the potassium channel, an X-ray crystal structure of a mammalian $Na_V$ has not been solved, due in large part to the difficulty in obtaining large quantities of the protein in a pure, correctly folded state (but see Payandeh et al., *Nature* 2011, 475, 353 for the crystal structure of a bacterial sodium channel). Towards that end, the structure of a bacterial homolog of $Na_V$ was recently reported (Nurani et al., *Biochemistry* 2008, 47, 8114-21), and subsequently was linked to a larger family of orthologs, forming a superfamily of proteins (Koishi et al., *J. Biol. Chem.* 2004, 279, 9532-9538). These proteins are believed to be involved in motility, chemotaxis and pH homeostasis (Ito et al., *Proc. Natl. Acad. Sci. U.S.A.* 2004, 101, 10566-10571). More recently, methods for generating milligram quantities of this protein have been reported (Nurani et al., *Biochemistry* 2008, 47, 8114-21). This bacterial homolog consists of only a single six transmembrane domain, which may form a functional unit as a tetramer, however its structural homology to the mammalian sodium channel is not yet clear.

Figure 3:
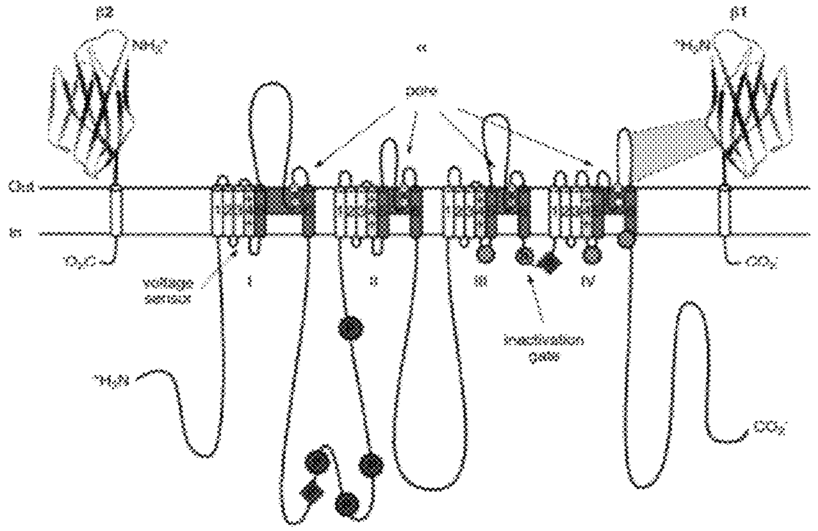
FIG. 3. Secondary structure of the voltage-gated sodium channel. The α-subunit is shown as with two associated β-subunits. Sites of protein phosphorylation, inactivation gate receptor, and inactivation particle IFM sequence are shown. Adapted from Catterall, *Neuron* 2000, 26, 13-25.

Insights into $Na_V$ structure have relied on a combination of primary sequence analysis, solution NMR analysis, homology modeling based on $K_V$, mutagenesis and toxin binding. Primary sequence analysis of $Na_V$ (Noda et al., *Nature* 1984, 312, 121-128; Guy et al., *Proc. Natl. Acad. Sci. U.S.A.* 1986, 508, 508-512) suggests that, like $K_V$, $Na_V$ is organized as a tetramer with four homologous domains, each containing six transmembrane α-helices (see FIG. 3). $Na_V$ is a single protein with each domain connected by a large intracellular loop. This so-called α-subunit contains all of the necessary components for a channel that activates and inactivates with changes in membrane potential, and is selective for $Na^+$. In neuronal cells, this α-subunit is generally associated with one or two β-subunits, which slightly alter the channel's gating characteristics. The α-subunit is heavily glycosylated, with carbohydrate comprising between 15%-30% of its molecular weight, and further post-translational modification occurs in the form of sulfation, acylation and phosphorylation (Schmidt et al., *J. Biol. Chem.* 1987, 262, 13713-13723). This molecular topology has been supported by extensive biochemical and electrophysiological studies (Catterall et al., *Neuron* 2000, 26, 13-25).

Figure 4:
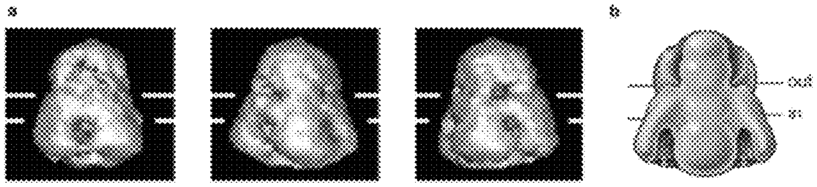
FIG. 4. Cryoelectron images of the voltage-gated sodium channel. (a) Surface representation of the sodium channel protein. (b) An adapted three-dimensional representation (Catterall et al., *Nature* 2001, 409, 988-991).

Cryo-electron microscopy has been used to obtain three-dimensional images of the $Na_V$ α-subunit at 19 Å resolution (Sato et al., *Nature* 2001, 409, 1047-1051). The images were acquired through single particle analysis of the solubilized protein, and signal to noise was improved by signal averaging of proteins that presented in similar orientations. The images show the expected 4-fold symmetry as well as, unexpectedly, a network of pores, one in each domain (see FIG. 4). Without intending to be bound by theory, it has been hypothesized that, like the potassium channel, a single ion-conducting pore exists through the axis of rotation about the four domains, and that the additional pores represent channels through which the voltage sensor in each domain may pass. The additional pores were not observed in any potassium crystal structure, however, and this hypothesis remains to be further substantiated. While these experiments provide a tantalizing glimpse of the macro-molecular features of the sodium channel, techniques delivering higher resolution will be required to develop a detailed understanding of the mechanical features of the sodium channel.

Two essential mechanical features of $Na_V$ are the ability to activate in response to membrane depolarization, and to inactivate rapidly thereafter. As with $K_V$, activation is coupled to movement of the positively charged S4, the voltage sensor, in the extracellular direction in all four protein domains. S4 contains 4, 5, 6, and 8 positively charged residues in D1, D2, D3 and D4, respectively, positioned at every third residue in the primary sequence (Yang et al., *Neuron* 1996, 16, 113-22). Studies of gating currents have shown that the equivalent of at least 10 positive charges must cross from the intracellular side of the membrane potential to the external side (Hirschberg et al., *J. Gen. Physiol.* 1995, 106, 1053-1068). The technique of cysteine scanning followed by intra/extracellular reaction with methanethiosulfonate reagents has shown that in S4/D4 two of the charged residues completely translocate from an intracellularly accessible position to an extracellularly accessible position, and a third charged moiety likely translocates partly through the membrane's potential difference (Yang et al., *Neuron* 1996, 16, 113-22). Multiplication of this charge movement among four domains accounts for measured gating currents.

Sodium channels must rapidly close following activation, a process that is not the microscopic reverse of activation, but instead leads to a unique, inactivated state. Defects in sodium channel inactivation lead to a variety of symptoms of neuronal hyperexcitability within the heart and throughout the central nervous system (Lehmann-Horn et al., *Phys. Rev.* 1999, 79, 1217-1372; Lehmann-Horn et al., *Pharma. News* 2001, 8, 29-36). The molecular mechanisms responsible for inactivation have been studied extensively (Ulbricht *Phys. Rev.* 2005, 85, 1271-1301). Inactivation appears to occur via occlusion of the channel pore from the cytoplasmic side of the membrane with a conserved sequence of three peptides—isoleucine-phenylalanine-methionine; known as the 1-F-M triad—found on the linker region between domains three and four (Bosmans et al., *Nature* 2008, 456, 202-208 and references therein). Solution state NMR spectroscopy studies (Rohl et al., *Biochemistry* 1999, 38, 855-861) reveal a helix-turn-latch motif, in which a flexible, conformationally mobile linker follows a stable helix. The linker is attached to a "latch", the I-F-M motif that appears to interact directly with the channel pore, forming a strong hydrophobic interaction that occludes the channel pore in the inactivated state.

The extracellular pore of the sodium channel is of tremendous interest since it is the binding site of the neurotoxins tetrodotoxin and saxitoxin, contains the components necessary to impart selectivity for sodium, and appears to be organized quite differently from the potassium channel. The $Na_V$ pore is comprised of the reentrant P-loops connecting S5 to S6 in each of the four protein domains (see FIG. 3) (Yu et al., *Genome Biol.* 2003, 4, 207.1-207.7). An "outer vestibule" consisting of glutamate-glutamate-methionine-aspartate (E-E-M-D) residues is conserved in all channel isoforms, and in contrast to the potassium channel, the selectivity filter in $Na_V$ consists of a single ring of four amino acids, an aspartate-glutamate-lysine-alanine (D-E-K-A) motif. This selectivity filter is consistent with an ion channel bearing a close phylogenetic relationship to calcium channels (Yu et al., *Pharmacol. Rev.* 2005, 57, 387-395), and indeed mutation of the D-E-K-A locus to E-E-E-E, as found in the voltage-gated calcium channel, confers the channel with calcium selectivity (Heinemann et al., *Nature* 1992, 356, 441-443; Favre et al., *Biophys. J.* 1996, 71, 3110-3125). This close relationship between $Na_V$ and $Ca_V$ channels suggests that structural insights into $Na_v$ may have implications for this broader family of voltage-gated ion channels. In further contrast to the potassium channel, the D-E-K-A locus appears to have some degree of motility during gating and in passing from the nonconductive state to the conductive one (Benitah et al., *J.*

*Neurosci.* 1999, 19, 1577-1585), and this molecular motion may be involved in slow inactivation (Xiong et al., *J. Gen. Physiol.* 2003, 122, 323-332). Finally, modeling studies suggest that it is not backbone carbonyls that make up the narrowest part of the channel pore, but in fact the amino acid side chains. Models of the channel pore are discussed further below.

The STX/TTX Binding Site

Sodium ion channels are requisite components of the systems that control respiration, cardiovascular function and motility in all life forms. Therefore, it is not surprising that this protein is the target of a diverse array of naturally occurring neurotoxins produced both by plant and animal species. It is also a highly studied drug target, as sodium channelopathies have been associated with arrhythmia, epilepsy, neuropathic pain, and congenital analgesia (Termin et al., *Annu. Rep. Med. Chem.* 2008, 43, 43-60, and references therein). At least six distinct neurotoxin receptor sites exist, and the effects of these neurotoxins range from block of sodium current to allosteric modulation of channel gating (Cestèle et al., *Biochimie* 2000, 82, 883-92).

Figure 5:
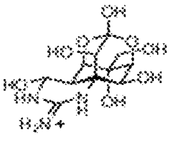
FIG. 5. Sodium channel pore blockers (−)-tetrodotoxin and (+)-saxitoxin.
Figure 5:
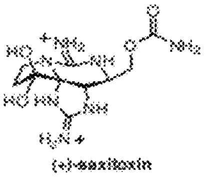

The extracellular pore of the sodium channel is believed to bind the neurotoxins saxitoxin (STX) and tetrodotoxin (TTX) (see FIG. 5) as well as the peptidic conotoxin. Each of these neurotoxins contains one or more guanidine moieties, a species to which the sodium channel is somewhat permeable (Hille, *J. Gen. Physiol.* 1971, 58, 599-619). Without intending to be bound by theory, it has been hypothesized that these guanidine moieties lodge themselves in the channel pore, with other functional groups in the molecules strategically located to hold the toxins in place through a series of strong hydrogen bonds and electrostatic interactions.

Mutagenesis studies strongly support the premise that residues comprising the outer vestibule and selectivity filter make up the TTX/STX receptor (Noda et al., *FEBS. Lett.* 1989, 259, 213-216; Terlau et al., *FEBS Lett.* 1991, 293, 93-96). This model is further supported by a recent report showing that clams that accumulate saxitoxin contain an outer vestibule E to D mutation, rendering these organisms largely insensitive to STX (Bricelj et al., *Nature* 2005, 434, 763-7). Only six of the nine sodium channel isoforms are TTX/STX sensitive. STX and TTX display a 200-5000-fold loss of potency against $Na_V$1.5, 1.8 and 1.9 (Backx et al., *Science* 1992, 257, 248-251; Heinemann et al., *Pflugers Arch.* 1992, 422, 90-92; Sivilotti et al., *FEBS Lett.* 1997, 409, 49-52). In the case of TTX, this sensitivity has been linked to a pi-cation interaction (Santarelli et al., *J. Biol. Chem.* 2007, 282, 8044-51) between the guanidine on the toxin and a tyrosine or phenylalanine residue located one position out (position 401 in $Na_V$1.4 numbering) from the aspartate in the selectivity filter D-E-K-A locus. In the insensitive $Na_V$ isoforms, this aromatic residue is instead a cysteine or serine; mutation of this residue to an aromatic moiety restores nanomolar binding affinity towards TTX (Satin et al., *Science* 1992, 256, 1202-1205).

The sodium channel has been the subject of intensive molecular modeling efforts with research directed primarily at two regions of the protein: the pore region, which includes the STX/TTX binding site, and the local anesthetic binding site, insight into which could provide for a more directed approach to developing new local anesthetics. The first computational pore model appeared more than 15 years ago from the laboratories of Lipkind and Fozzard (Lipkind et al., *Biophys. J.* 1994, 66, 1-13). Operating under the assumption that the selectivity filter must comprise the narrowest part of the sodium channel pore, and using mutagenesis data that had implicated residues in the selectivity filter and outer vestibule as the STX/TTX binding site, the authors took very short segments of each of the four p-loops—positions −7 to +6 from the selectivity filter—and arranged them around rigid STX and TTX molecules. Removal of the toxins from the model resulted in a funnel-like structure that expanded outwards from the selectivity filter.

It is not currently possible to unambiguously assign orientations to STX and TTX at their binding sites in the $Na_V$ channel pore, as no direct experimental evidence yet exists to support such a hypothesis. Nevertheless, alignment of the STX 7,8,9-guanidine with that of TTX results in overlap of the STX hydrated ketone with the C-9, C-10 diol in TTX, functional groups that are believed to be important hydrogen bond donors in the protein-toxin complex. This binding pose has been supported by mutant cycle analysis (Penzotti et al., *Biophys. J.* 1998, 75, 2647-57; Penzotti et al., *Biophys. J.* 2001, 80, 698-706).

Following $K^+$ channel structural studies reported by MacKinnon (Doyle et al., *Science* 1998, 280, 69-77), Lipkind and Fozzard further refined their model of the sodium channel pore, using the Kcsa crystal structure to predict the location of the S5 and S6 helices (Lipkind et al., *Biochemistry* 2000, 39, 8161-8170; Khan et al., *J. Physiol.* 2002, 543, 71-84). The authors model the S5-S6 P-loop as an α-helix-turn-β-strand motif, and unlike the potassium channel, model the amino acid side chains, rather than backbone carbonyls, interacting with sodium ions in the selectivity filter. The outer vestibule residues stabilize and dehydrate sodium ions as they enter the channel pore.

Figure 6:
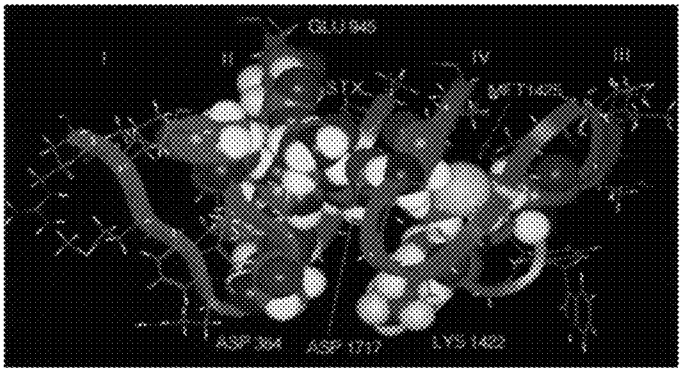
FIG. 6. Lipkind and Fozzard's model of STX bound in the $Na_V$ channel pore.

The Lipkind and Fozzard $Na_V$ pore model successfully capitulates much of the experimental mutagenesis data, as regards the residues that comprise the selectivity filter, outer vestibule and STX/TTX binding site (see FIG. 6). Explicit in the design of this model is the necessity to reposition the axes of the pore helices relative to the Kcsa structure. This repositioning is necessary because in the potassium channel, backbone carbonyls line the pore, interacting with $K^+$ ions as they pass through the pore. In sodium channels, on the other hand, the side chains of the selectivity filter residues interact with ions passing through the pore. In the Lipkind and Fozzard $Na_V$ model, in order to accommodate inward pointing side chains of the pore residues, the axes of the pore helices had to be shifted outward. Spacial shifting of these pore helices is problematic, however, when one considers that the sodium channel protein is made up of a densely packed array of α-helices—shifting the pore helices in space would require a significant reorganization of the entire protein.

Figure 7:
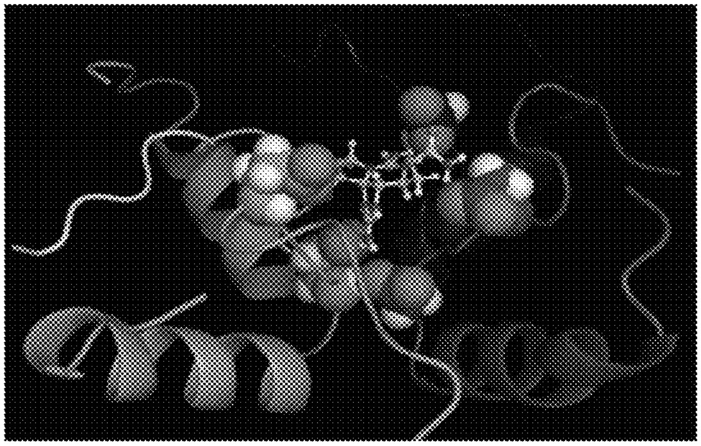
FIG. 7. A model of the P-loop region of the $Na_V$ channel (Tikhonov et al., *Biophys. J.* 2005, 88, 184-197). Bound STX is shown as a ball and stick model, while purported toxin-binding residues (Noda et al., *FEBS. Lett.* 1989, 259, 213-216; Terlau et al., *FEBS Lett.* 1991, 293, 93-96) are shown as space filling models. D1 (bottom, right, front), D2 (bottom, left, front), D3 (top, left, back), D4 (top, right, back).

Zhorov and Tikhonov have constructed a sodium channel pore in which the axes of the pore helices are constricted in an arrangement exactly analogous to the MthK $K^+$ bacterial potassium channel (Tikhonov et al., *Biophys. J.* 2005, 88, 184-197). The selectivity filter residues were shaped around rigid STX and TTX molecules and subjected to Monte Carlo minimization. In the resulting pore model, which consisted of the pore helix, a turn, and the selectivity filter region (see FIG. 7), the selectivity filter region was significantly altered from the MthK $K^+$ bacterial potassium channel; the pore helices were constricted in space exactly as in the MthK $K^+$ structure. The resulting pore was almost identical whether STX or TTX was used through Monte Carlo minimization process. Docking of several deoxygenated TTX derivatives, including 11-deoxyTTX, 4,9-anhydroTTX, and 5,6,11-trideoxyTTX, resulted in differential binding energies consistent with experimentally derived values, and produced a pore that was permeable to guanidinium.

The Zhorov and Tikhinov P-loops model of the sodium channel pore suggests a binding interaction between tyrosine 401 ($rNa_V$1.4 numbering) and the hydrophobic side of TTX.

The identity of the residue at position 401 is known to affect the sensitivity of each $Na_V$ isoform to block by STX and TTX; STX and TTX display a 200- to 5000-fold loss of potency against $Na_V$ isoforms in which residue 401 is not aromatic (Backx et al., *Science* 1992, 257, 248-251; Heinemann et al., *Pflugers Arch.* 1992, 422, 90-92; Sivilotti et al., *FEBS Lett.* 1997, 409, 49-52). A recent report by Dougherty and coworkers, however, suggests that the nature of this interaction is not hydrophobic, but is better represented as a cation-pi interaction (Santarelli et al., *J. Biol. Chem.* 2007, 282, 8044-51). Scheib and coworkers have built a computational model that incorporates this finding, specifically accounting for this cation-pi interaction (Scheib et al., *J. Mol. Model.* 2006, 12, 813-22). Isoforms $Na_V$1.2 and $Na_V$1.8 (TTX potencies of 12 nM and 60 μM, respectively; position 401 is phenylalanine and serine, respectively) were used to build the model. Docking of TTX into the pore of each isoform resulted in TTX's 1,2,3-guanidinium contacting the respective position 401 residues of the two channel isoforms. In $Na_V$1.2, phenylalanine 401 and a tryptophan residue in domain 2 formed a V-shaped pocket, well-oriented to stabilize the positive charge character of TTX's 1,2,3-guanidine. In $Na_V$1.8, this V-shaped substructure was absent, and no binding interaction was observed. The Scheib model shows one way in which an aromatic residue at this key position may be oriented to interact with TTX's 1,2,3-guanidinium to generate a favorable binding interaction.

Comparison of the various models that have been reported describing the binding event between TTX and STX and the $Na_V$ pore shows that the differences between these models are subtle. Each model fits an impressive array of biochemical data related to toxin binding. Nevertheless, direct evidence (e.g. e.g. photoaffinity labeling) of how site I neurotoxins are oriented in the sodium channel pore, and ultimately how the channel pore is structured, remains unavailable.

The β-Subunits

While the $Na_V$ α-subunit contains all of the machinery necessary to form a functional and selective ion channel, complexation with one or two β-subunits has subtle but important effects on gating and on channel expression at the plasma membrane. There are three known β-subunits (β1-β3), as well as a fourth that is a splice variant of β1. β1 and β3 are noncovalently bound to the α-subunit, while β2 and β4 form disulfide bonds to the α-subunit (Catterall et al., *Neuron* 2000, 26, 13-25). Sodium channels in skeletal muscle generally only contain the β1 subunit, whereas other isoforms may contain any of the β subunits. The β-subunits are much smaller than the α-subunits with molecular weights around 45 kDa. These proteins are comprised of a single transmembrane segment, with a large extracellular amino terminus and a smaller intracellular carboxy terminus.

Sodium channel β-subunits play an important role in modifying channel gating with respect to both the voltage dependence and kinetics of activation and inactivation (Isom, *Neuroscientist* 2001, 7, 42-54 and references therein). For example, when the β1 subunit is coexpressed with the $Na_V$ skeletal muscle α-subunit, activation and inactivation rates are increased and more closely resemble gating characteristics observed in native tissue (Isom et al., *Neuron* 1994, 12, 1183-1194; Isom et al., *J. Biol. Chem.* 1994, 270, 3306-3312). Importantly, the gating characteristics of $Na_V$ as well as its modulation by β-subunits are dependent on the particular heterologous host in which the proteins are expressed (Isom, *Neuroscientist* 2001, 7, 42-54 and references therein). For example, $Na_V$1.4 gates relatively slowly when expressed in Xenopus oocytes, and addition of the β1 subunit results in major changes to channel gating kinetics. When these same channels are expressed in mammalian fibroblasts, addition of the β1 subunit has little effect on gating kinetics.

$Na_V$ β-subunits also play an important role in channel expression at the plasma membrane (see also below). Structurally, the large extracellular N-terminus likely adopts an immunoglobulin fold and bears sequence homology with the L1 family of cell adhesion molecules (CAMs) that modulate cell-cell interactions and cell adhesion (Isom et al., *Cell* 1995, 83, 433-442; Isom et al., *Nature* 1996, 383, 307-308). These subunits are involved in critical aspects of protein shuttling to the plasma membrane and likely are involved in clustering of sodium channels at nodes of Ranvier. Mutations in $Na_V$ β-subunits have been linked to epilepsy, long QT syndrome, and neuropathic pain, and present a likely future target of pharmacological modulation (Isom, *Neuroscientist* 2001, 7, 42-54 and references therein; Tseng et al., *J. Mol. Microbiol. Biotechnol.* 2007, 12, 249-62).

Regulation and Trafficking of $Na_V$

The trafficking of sodium channels and their expression at the cell membrane is a tightly controlled process dependent on association with multiple proteins through protein-protein interactions (Cusdin et al., *Traffic* 2008, 9, 17-26). The full arsenal of proteins responsible for this process has not been elucidated, however association with β-subunits and with other trafficking proteins substantially increases the rate at which sodium channels are processed through the secretory pathway. In neurons, sodium channels covalently associate with β2-subunits in a post-Golgi compartment and are shuttled to the cell membrane. About 70% of sodium channels lack an associated β2-subunit, and these uncomplexed α-subunits are located primarily in the cytoplasm; complexation and trafficking are likely the rate limiting steps for expression at the plasma membrane (Schmidt et al., *Cell* 1986, 46, 437-444). Association with contactin, a glycosoyl-phosphatidylinositol-anchored CAM protein, also facilitates expression at the plasma membrane (Liu et al., *J. Biol. Chem.* 2001, 276, 46553-46561; Shah et al., *J. Neurosci.* 2004, 24, 7387-7399; Kazarinova-Noyes et al., *J. Neurosci.* 2001, 21, 7517-7525).

Proper localization of all of the components of neuronal signaling, including sodium channels, potassium channels, and $Na^+/K^+$-ATPase is of crucial importance in myelinated neurons. Two regions of the neuron are particularly important with respect to signaling: the nodes of Ranvier and the axon initial segment (AIS, also called the axon hillock). Nodes of Ranvier contain very high concentrations of sodium channels, with densities up to 12,000 channels/$\mu m^2$ reported, and 700,000 channels at a single node (Ritchie et al., *Proc. Natl. Acad. Sci. U.S.A.* 1977, 74, 211-215). Conversely, the regions of membrane that contact myelin contain no more than 25 channels/$\mu m^2$. This arrangement of $Na_V$ channels is central to saltatory conduction (Ritchie et al., *Proc. Natl. Acad. Sci. U.S.A.* 1977, 74, 211-215).

Localization of $Na_V$ channels at nodes of Ranvier and at the AIS is a tightly controlled process that involves three basic components: regulated export of channels from the ER (as discussed above); uniform expression at the cell membrane with selective localized retention; and regulated endocytosis. Many of the same processes that control clustering at nodes of Ranvier are operative at the AIS. The primary $Na_V$ isoforms expressed at these two locations are $Na_V$1.2 and $Na_V$1.6. These sodium channel isoforms are initially inserted uniformly into the plasma membrane, where they freely diffuse (Garrido et al., *Biol. Cell* 2003, 95, 437-445). Diffusion at nodes of Ranvier and at the AIS, however, is tightly restricted, and $ankyrin_G$ and spectrin βIV proteins are believed to anchor sodium channels at these locations. Both of these proteins are known to associate with the cell's underlying actin cytoskeleton (Bennett et al., *Physiol. Rev.* 2001, 81, 1353-1392).

The myelin sheath itself plays a pivotal role in $Na_V$ regulation and clustering. Clusters of $Na_V$ channels begin to develop immediately after glial cells attach themselves to axons, and these clusters appear to translocate along the length of the axon as the myelinating glial cell grows (Dugandzija-Novakovic et al., *J. Neurosci.* 1995, 15, 492-503; Vabnick et al., *J. Neurosci.* 1996, 16, 4914-4922; Vabnick et al., *J. Neurobiol.* 1998, 37, 80-96). While both $Na_V$1.2 and 1.6 are initially expressed in neurons, as myelination occurs $Na_V$1.2 is selectively replaced at nodes of Ranvier with $Na_V$1.6 (Boiko et al., *Neuron* 2001, 30, 91-104). Neither clustering nor upregulation occur in mice that lack myelin basic protein (Koszowski et al., *J. Neurosci.* 1998, 18, 5859-5868), a protein involved in the myelination of neurons in the CNS. Finally, gliomedin, a protein secreted by Schwann cells, contains a CAM binding site and appears to concentrate at the nodal edge of Schwann cells, providing high avidity binding sites for CAMs along with their associated sodium channel β- and α-subunits (Eshed et al., *Neuron* 2005, 47, 215-229).

The rate of turnover of sodium channels in vivo is not precisely known but is believed to be on the order of 1-3 days (Ritchie, *Proc. R. Soc. London* 1988, 233, 423-430). Trafficking is a dynamic process, with delivery of $Na_V$ proteins to the plasma membrane balanced by degradation of existing proteins. Therefore, sodium channel proteins must be continuously trafficked from ribosomes in the soma, along the length of the axon, to the site of insertion in the plasma membrane. The mechanisms that govern selectivity in the process of endocytosis are not known. Nevertheless, both sustained activation of $Na_V$ (Paillart et al., *J. Cell Biol.* 1996, 134, 499-509) and elevated intracellular $Ca^{2+}$ concentration (Kobayashi et al., *Ann. N.Y. Acad. Sci.* 2002, 971, 137-134) appear to lead to increased $Na_V$ endocytosis.

In summary, the regulation, trafficking and subcellular localization of $Na_V$ relies on the association of the $Na_V$ α-subunit with one or more β-subunits, which, in combination with other trafficking proteins, control the rate of expression at the cell membrane. The proteins are distributed uniformly at the cell membrane, then selectively clustered at the AIS and at nodes of Ranvier. Understanding the rate of turnover of $Na_V$ channels and the cofactors that govern selective endocytosis represent current areas of research.

$Na_V$ Isoform Distribution

Nine different voltage-gated sodium channel isoforms have been identified and cloned, and the sequence homology between all isoforms is >50%. The biological relevance of sequence variation among different $Na_V$ isoforms and splice variants is generally attributed to three functional advantages (Caldwell et al., *Adv. Mol. Cell. Biol.* 2004, 32, 15-50): each isoform possesses unique signaling characteristics which are appropriate for certain tissue types; different sequences may allow each channel to be recruited and transported by appropriate trafficking molecules; and the unique, non-coding regions may play a role in channel regulation, affecting expression. Nearly all tissues contain more than a single $Na_V$ isoform, the possible exceptions being mature skeletal muscle and cardiac muscle, which express fairly pure populations of $Na_V$1.4 and 1.5, respectively. Nevertheless, some level of tissue isoform specificity exists, and a general understanding of where each isoform is distributed has developed (Table 1).

TABLE 1

The isoform distribution of voltage-gated sodium channels (adapted from: Catterall et al., *Pharmacol. Rev.* 2005, 57, 397-409; see also references therein)

| $Na_V$ isoform | STX sensitive?[a] | Distribution |
|---|---|---|
| 1.1 | Yes | Central neurons: primarily localized to cell bodies; cardiac myocytes |
| 1.2 | Yes | Central neurons: primarily localized to unmyelinated and premyelinated axons |
| 1.3 | Yes | Central neurons primarily expressed in embryonic and early prenatal life; preferentially localized in cell bodies in adult rat brain; cardiac myocytes |
| 1.4 | Yes | High levels in adult skeletal muscle and low levels in neonatal skeletal muscle |
| 1.5 | No | Cardiac myocytes, immature and denervated skeletal muscle, certain brain neurons |
| 1.6 | Yes | Somatodendritic distribution in output neurons of the cerebellum, cerebral cortex, and hippocampus; Purkinje cells in the cerebellar granule cell layer; brainstem and spinal cord, astrocytes, and Schwann cells; DRG; nodes of Ranvier of sensory and motor axons in the PNS; nodes of Ranvier in the CNS |
| 1.7 | Yes | All types of DRG neurons, sympathetic neurons, Schwann cells, and neuroendocrine cells |
| 1.8 | No | Small and medium-sized DRG neurons and their axons |
| 1.9 | No | C-type DRG neurons, trigeminal neurons and their axons; preferentially expressed in nociceptive DRG neurons |

[a]STX displays single digit nanomolar $IC_{50}$s against sensitive $Na_V$ isoforms, while insensitive isoforms are 200-5000-fold less sensitive.

Sodium channels are found in certain sensory receptors, including those for pain, taste, and sound, where they serve to amplify and transduce sensory information. Some $Na_V$ isoforms appear to have tissue specific distributions, and several isoform specific sodium channelopathies lead to tissue specific dysfunction. For example, mutations in $Na_V$1.4 have been linked with periodic paralysis (Lehmann-Horn et al., *Physiol. Rev.* 1999, 79, 1317-1372), which is caused by a defect in $Na_V$ inactivation, resulting in channels experiencing prolonged conductance. Without intending to be bound by theory, prolonged conductance is believed to lead to a slow inactivated state, which is mechanistically distinct from fast inactivation and is poorly understood. Recovery from this state is very slow, causing the channels to remain nonconductive for extended periods of time. Individuals displaying this phenotype do not have cognitive deficits or cardiac disorders, which is consistent with a singular location of $Na_V$1.4 within skeletal muscle. Other isoform specific channelopathies include long QT syndrome (Wang et al., *Cell* 1995, 80, 805-811) and disorders of the central nervous system, including paralysis, ataxia, and dystonia (Kohrman et al., *J. Neurosci.* 1996, 16, 5993-5999; Sprunger et al., *Hum. Mol. Genet.* 1999, 8, 471-479). Similarly, gain of function mutation in $Na_V$1.7 has been linked to paroxysmal extreme pain disorder, a condition characterized by burning pain in the rectal, ocular or submandibular regions accompanied by skin flushing (Fertleman et al., *Neuron* 2006, 52, 767-774).

$Na_V$ and Pain

The relationship between pain perception and sodium channel expression is a highly active area of current research. The signaling mechanisms that are involved in transmitting pain sensation are closely tied to sodium channel expression (for reviews, see: Amir et al., *J. Pain* 2006, 7, Supp. 3, S1-29; Devor et al., *J. Pain* 2006, 7, Supp. 1, S3-S12; Cummins et al., *Pain* 2007, 131, 243-57). Central to pain signaling is the ability of neurons to fire repetitive bursts of action potentials. In chronic pain conditions, signaling occurs as a result of a reorganization of the components that integrate and send signals both in the central and peripheral nervous system (Devor et al., *J. Pain* 2006, 7, Supp. 1, S3-S12). At least three separate processes that involve $Na_V$ define this reorganization: changes in gene expression; changes in trafficking and accumulation of $Na_V$; and altered $Na_V$ kinetics.

Recent studies have focused on the contribution of individual sodium channel isoforms to pain perception. Four sodium channel isoforms ($Na_V$1.3, 1.7, 1.8 and 1.9) have displayed altered expression profiles in studies of chronic pain, and a variety of genetic and small molecule (Hoyt et al., *Bioorg. Med. Chem. Lett.* 2007, 17, 4630-4634; Jarvis et al., *Proc. Natl. Acad. Sci. U.S.A.* 2007, 104, 8520-8525) interventions have continued to probe their contributions (for a recent review, see: Krafte et al., *Curr. Opin. Pharmacol.* 2008, 8, 50-56).

Peripheral nerve injury is known to cause upregulation of $Na_V$1.3. A recent study utilized genetic knockdown to examine if this channel isoform contributes to development and maintenance of chronic pain. In spared nerve injury and nerve axotomy rat pain models, upregulation of $Na_V$1.3 was observed, however genetic knockdown of $Na_V$1.3 after injury did not alleviate behaviors associated with hypersensitivity (Lindia et al., *Pain* 2005, 117, 145-153).

Congenital indifference to pain is a rare inherited condition in which patients have a severely decreased ability to sense pain, while maintaining otherwise normal sensory and motor function. Two studies of families expressing this phenotype showed a series of loss-of-function mutations in the SCN9A gene, which encodes for $Na_V$1.7 (Goldberg et al., *Clin. Genet.* 2007, 71, 311-319; Ahmad et al., *Hum. Mol. Genet.* 2007, 16, 2114-2121). Following up on this result, Wood and co-workers generated global $Na_V$1.7-null mice, however these animals died shortly after birth. The difference in phenotype between mice and humans is attributed to species-specific variation in channel distribution. The authors therefore utilized the technique of nociceptor-specific gene ablation in which $Na_V$1.7 was knocked out selectively in nociceptors (Nassar et al., *Proc. Natl. Acad. Sci. U.S.A.* 2004, 101, 12706-12711). These animals exhibited increased mechanical and thermal pain thresholds, and almost complete ablation of response to inflammatory pain.

$Na_V$1.8 has been an important target for both genetic and small molecule studies since it is expressed preferentially in peripheral sensory neurons. Genetic knockout of $Na_V$1.8 in mice produced viable, fertile and apparently normal animals. Consistent with $Na_V$1.8's role in nociception, these mice showed significantly decreased response to noxious mechanical stimuli and some types of inflammatory pain (Akopian et al., *Nature Neurosci.* 1999, 2, 541-549; Laird et al., *J. Neurosci.* 2002, 22, 8352-8356), however they did not display behavioral changes in neuropathic pain (Kerr et al., *NeuroReport* 2001, 12, 3077-3080). Isolation of sensory neurons in these animals showed increased current densities of TTX-sensitive channels, which suggests that a compensatory mechanism causes upregulation of other $Na_V$ isoforms. Contrasting these results, genetic knockdown of $Na_V$1.8 in a rat model of neuropathic pain by antisense oligodeoxynucleotides resulted in a reversal of neuropathic pain induced by spinal nerve injury without affecting normal sensory response (Lai et al., *Pain* 2002, 95, 143-152). More recently, siRNA was used to selectively knock down $Na_V$1.8 expression in rats displaying mechanical allodynia due to chronic constriction nerve injury (Dong et al., *Neuroscience* 2007, 146, 812-821). These rats displayed robust reversal of mechanical allodynia, and knockdown of $Na_V$1.8 in vivo was confirmed by measuring $Na_V$1.8 mRNA expression.

$Na_V$1.9 is also expressed preferentially in nociceptors of the peripheral nervous system, and $Na_V$1.9 null mutant nice have been utilized in models of mechanical, thermal and inflammatory pain. In one study these animals were found to be viable but did not show mechanical or thermal hypersensitivity after nerve injury or inflammation (Priest et al., *Proc. Nat. Acad. Sci. U.S.A.* 2005, 102, 9382-9387). In a second study, administration of prostaglandin $E_2$, bradykinin, interleukin-1β, capsaicin, and $P2X_3$ and P2Y, agents known to elicit an inflammatory response, $Na_V$1.9 null mutant mice showed decreased pain hypersensitivity, while normal thermal and mechanical pain responses were unchanged (Amaya et al., *J. Neurosci.* 2006, 26, 12852-12860). Collectively, these studies suggest that $Na_V$1.9 plays a role in inflammation-induced hypersensitivity of peripheral nerves.

Taken together, genetic knockdown and knockout studies indicate an important role for several sodium channel isoforms in pain signaling. Isoform signature appears to vary with the different types of pain (i.e. inflammatory vs. neuropathic). While these studies implicate certain channel isoforms in the pain response cycle, they are not instructive in terms of the precise trafficking events that must take place when a neuron's signaling characteristics are altered. All of the $Na_V$ isoforms that have been implicated in chronic pain are also present before injury. An understanding of the precise regulatory, trafficking and reorganization events that lead to altered neuronal signaling would offer mechanistic insight into pain development.

Fluorescence Techniques for Visualizing $Na_V$

Interest in the relationship between $Na_V$ and neuronal excitability has led to the development of fluorescence techniques for visualizing sodium channel proteins. A singular example of an $Na_V$-GFP fusion protein was reported in 2002. The c-terminus of the human heart sodium channel (hH1) was labeled with GFP and this construct was successfully transfected into HEK293 cells, displaying identical electrophysiological properties to the wild type protein (Zimmer et al., *J. Membr. Biol.* 2002, 186, 1-12). Examination of the heterologously expressed fusion protein by confocal microscopy revealed high levels of expression in several intracellular membranes, particularly within the endoplasmic reticulum (ER). It was proposed that the ER may serve as a reservoir for cardiac sodium channels, and that transport out of the ER may be the rate-limiting step to expression at the cell membrane.

Figure 8:
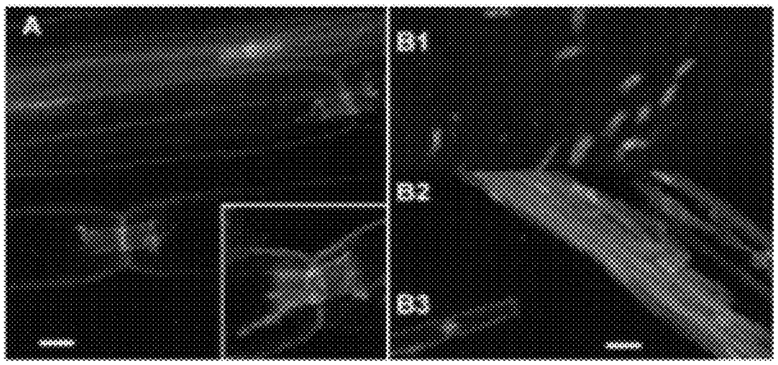
FIG. 8. Immunofluorescent images (Caldwell et al., *Proc. Nat. Acad. Sci. U.S.A.* 2000, 97, 5616-5620) of fixed rat and mouse sciatic nerve. (A) Rat sciatic nerve labeled with $Na_V$1.6 specific antibody. (B) Mouse sciatic nerve labeled with $Na_V$1.6 specific antibody. (B1) Wild-type mouse, (B2) $Na_V$1.6 null mutant mouse and (B3) wild-type node preincubated with anti-$Na_V$1.6 antibody.

Antibodies specific for each of the nine $Na_V$ isoforms have been developed, and these tools have helped to further elucidate the distribution of $Na_V$ isoforms in various types of tissues, and at specific locations within a given axon. For example, Levinson and coworkers have shown through isoform specific labeling of fixed nerve tissue that $Na_V$ 1.6 is expressed preferentially at nodes of Ranvier in both sensory and motor axons in the peripheral nervous system, and at nodes of Ranvier in the CNS (see FIG. 8) (Caldwell et al., *Proc. Nat. Acad. Sci. U.S.A.* 2000, 97, 5616-5620).

Several other studies out of the Levinson lab have shown altered sodium channel isoform distribution in developing neurons (Kaplan et al., *Neuron* 2001, 30, 105-119) and in neurons displaying myelination disease states (Ulzheimer et al., *Mol. Cell. Neurosci.* 2004, 25, 83-94). More recently, Levinson and coworkers have used wisdom tooth dental pulp (Henry et al., *J. Pain* 2009, 10, 750-758) to study the correlation between pain prior to tooth extraction and expression of $Na_V$1.7 (Luo et al., *Mol. Pain* 2008, 4, 16-39) and 1.8 (Henry et al., *Neurosci. Lett.* 2005, 380, 32-36). Finally, Levinson has shown differences in $Na_V$1.2 and $Na_V$1.6 at axon initial segments in myelinated vs. non-myelinated axons (Boiko et al., *J. Neurosci.* 2003, 23, 2306-2313). Taken together, these studies show the power of fluorescence techniques and immunohistology in understanding $Na_V$ regulation and distribution.

The ability to perform similar experiments in live organisms would allow for observation of the dynamic processes involved in $Na_V$ trafficking, and such is the motivation for development of additional tools for labeling these channels.

In summary, our understanding of the structural mechanics involved in sodium channel molecular function has continued to evolve over the past 15 years, even in the absence of X-ray crystallographic information. Techniques as diverse as synthesis, NMR and protein mutagenesis continue to illuminate the precise structural elements by which nature has designed this exquisitely selective machine for passing ions through the cell membrane.

Regulation, trafficking and localization of $Na_V$ represent vital processes that control the electronic properties of excitable cells. The precise regulatory mechanisms involved in maintaining these processes are not fully understood, however current efforts utilizing immunohistology as a means of visualizing channel expression at the plasma membrane have illuminated distinct changes in expression profiles of individual $Na_V$ isoforms in various pain states.

The challenge of visualizing changes in sodium channel expression in live tissue remains a complex problem with much promise in the potential to illuminate fundamental mechanisms of neuronal excitability. Selective blockade of aberrant sodium current likewise represents a possible solution to diseases of hyperexcitability. Within this context, the development of high affinity small molecule inhibitors of $Na_V$ could provide a fruitful approach to augmenting our understanding of both of these processes.

Compounds

According to one aspect of the invention, novel compound derivatives of aconitine are provided. The structures of the compounds may be represented by the general formula (II):

(II)

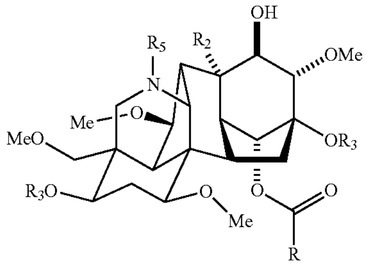

or a pharmaceutically acceptable salt or prodrug thereof, wherein:

R is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

$R_2$ is alkyl, alkoxy, or,

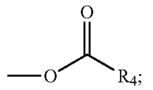

each $R_3$ is independently hydrogen or a protecting group;

each $R_4$ is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamindo, or azido; and $R_5$ is alkyl;

provided that, when R is unsubstituted phenyl, $R_2$ is

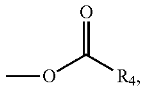

and each $R_3$ is hydrogen, then $R_4$ is not alkyl or alkenyl; and when R is p-methoxyphenyl, $R_2$ is

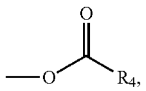

and each $R_3$ is hydrogen, then $R_4$ is not methyl.

As used herein, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

As used herein, the term "alkoxy" refers to an alkyl group, in certain specific embodiments, a lower alkyl group, having an oxygen attached thereto. Representative alkoxy groups include methoxy, ethoxy, propoxy, tert-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, cycloalkyl, heterocyclyl, aryl, or heteroaryl groups is contemplated.

The term "$C_{x-y}$" when used in conjunction with a chemical moiety, such as, acyl, acyloxy, alkyl, alkenyl, alkynyl, or alkoxy, is meant to include groups that contain from x to y carbons in the chain. For example, the term "$C_{x-y}$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

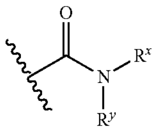

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g. e.g., a moiety that can be represented by

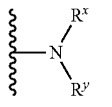

or

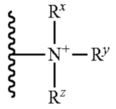

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Aryl groups also include benzopyran moieties, including keto-substituted benzopyran moieties, such as, for example, coumarinyls and related compounds.

The term "carbamate" is art-recognized and refers to a group

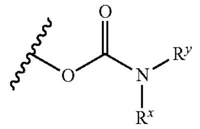

or

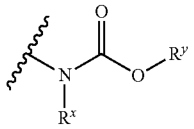

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group —$OCO_2$—$R^x$, wherein $R^x$ represents a hydrocarbyl group.

The term "carboxy", as used herein, refers to a group represented by the formula —$CO^2H$.

The term "ester", as used herein, refers to a group —C(O)$OR^x$ wherein $R^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O- heterocycle. Ethers include "alkoxyalkyl" groups, which may be represented by the general formula alkyl-O-alkyl.

The term "guanidinyl" is art-recognized and may be represented by the general formula

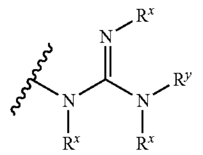

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group $—OSO_3H$, or a pharmaceutically acceptable salt thereof.

The term "sulfonamide" is art-recognized and refers to the group represented by the general formulae

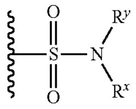

or

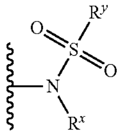

wherein $R^x$ and $R^y$ independently represent hydrogen or hydrocarbyl.

The term "sulfoxide" is art-recognized and refers to the group —S(O)—$R^x$, wherein $R^x$ represents a hydrocarbyl.

The term "sulfonate" is art-recognized and refers to the group —$SO_3H$, or a pharmaceutically acceptable salt thereof.

The term "sulfone" is art-recognized and refers to the group —$S(O)_2$—$R^x$, wherein $R^x$ represents a hydrocarbyl.

The term "thioalkyl", as used herein, refers to an alkyl group substituted with a thiol group.

The term "thioester", as used herein, refers to a group —C(O)S$R^x$ or —SC(O)$R^x$ wherein $R^x$ represents a hydrocarbyl.

The term "thioether", as used herein, is equivalent to an ether, wherein the oxygen is replaced with a sulfur.

The term "urea" is art-recognized and may be represented by the general formula

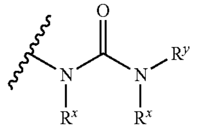

wherein $R^x$ and $R^y$ independently represent hydrogen or a hydrocarbyl.

According to some embodiments of the invention, in compounds of structural formula (II), each $R_3$ is hydrogen.

According to some embodiments of the invention, the $R_2$ group of structural formula (II) is

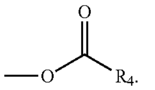

In preferred embodiments of the invention, the $R_4$ group is alkyl.

In even more preferred embodiments, the $R_4$ is methyl.

According to some embodiments of the invention, the $R_5$ group is methyl or ethyl, and in preferred embodiments, $R_5$ is ethyl.

In some embodiments of the invention, the R group of structural formula (II) is alkyl, aryl, or cycloalkyl, and is optionally substituted with 1 to 3 A groups.

In some embodiments of the invention, the R group is alkyl, phenyl, naphthyl, cyclohexyl, or coumarinyl, and is optionally substituted with 1 to 3 A groups.

In certain embodiments, the A groups are independently alkyl, alkoxyl, halo, trihalomethyl, or azido.

In preferred embodiments, R is aryl, heteroaryl, or cycloalkyl, and is optionally substituted.

In specific embodiments, the R group of structural formula (II) is selected from any one of the following:

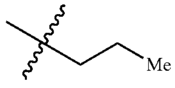

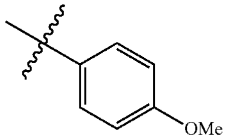

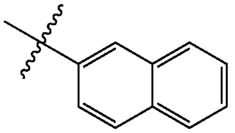

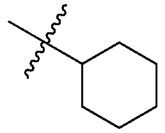

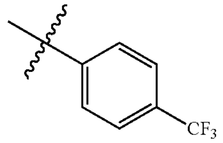

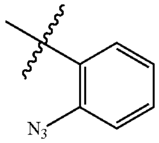

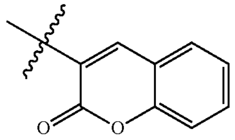

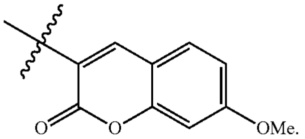

In even more specific embodiments, the R group is

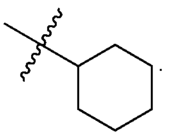 [SMILES: *C1CCCCC1]

In some embodiments of the invention each $R_3$ of structural formula (II) is a protecting group.

One of ordinary skill in the art would understand that a protecting group is reversibly attached to a desired position of the molecule to control the reaction of other agents at that position. Protecting groups useful in the practice of the instant invention are well known in the art. See, for example, "Greene's Protective Groups in Organic Synthesis, $4^{th}$ edition", by P. G. M. Wuts and T. W. Greene (Wiley-Interscience, 2006); and "Protecting Groups", by P. Kocienski (Thieme, 2005). For purposes of the instant invention, an acetyl group is not considered a protecting group.

In preferred embodiments of the invention, the protecting group used is a silyl protecting group.

In more preferred embodiments, the protecting group is t-butyldimethylsilyl or trimethylsilyl.

In even more preferred embodiments, the protecting group is trimethylsilyl.

In some embodiments, the compound of the invention modulates the activity of a sodium channel. As described above, the sodium channel is a highly studied drug target, as sodium channelopathies have been associated with arrhythmia, epilepsy, neuropathic pain, and congenital analgesia. Modulation of the sodium channel activity by the compounds of the instant invention may therefore provide a therapeutic benefit to patients suffering such conditions. See, for example, Tsuchida et al., The Effect of Chinese Herbal Medicine Containing Aconitine on the Pain Relief in Interstitial Cystitis Patients—a Preliminary Study. *J. Urology* 2009, 181, 23-24, and references therein; Ameri, A. The Effects of *Aconitum* Alkaloids on the Central Nervous System. *Progress in Neurobiology* 1998, 56, 211-235.

In certain embodiments, the compounds of the instant invention cause the sodium channel to open. In specific embodiments, the compounds cause the sodium channel to open at a lower membrane potential than aconitine. In some embodiments, the compounds of the invention cause decreased flow of sodium through the sodium channel. Without intending to be bound by theory, these effects on the sodium channel may be responsible for the therapeutic benefits provided to patients by these compounds.

The biological and pharmacological activity of the compounds of the invention can be assessed by a variety of experimental methods, as are well known by those of ordinary skill in the art. For example, the activity of the instant compounds in modulating channel activity of the sodium channel may be measured using whole cell or other types of electrophysiological methods. See, for example, Hille, *Ion Channels of Excitable Membranes,* 3rd ed., 2001, Sinauer Associates: Sunderland, Mass.; Sakmann and Neher (eds), *Single Channel Recording,* 1995, Plenum Press, New York and London; and the references provided therein. The effects of the instant compounds on neuropathic or nociceptive pain may, for example, be assessed by subjecting the plantar surface of rats to a series of von Frey monofilaments to determine the mechanical withdrawal threshold (MWT). See, for example, Ou et al., *Neurochem. Int'l.* 2011, 58, 564-573. Other related and unrelated methods may likewise be usefully employed to assess the activity of the instant compounds.

Pharmaceutical Compositions

In another aspect, the instant invention provides pharmaceutical compositions comprising a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See Remington: The Science and Practice of Pharmacy, 20th ed. (Alfonso R. Gennaro ed.), 2000.

A pharmaceutical composition containing a compound of the instant invention may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations of the present invention may conveniently be presented in unit dosage form and may be prepared by any methods well known in the art of pharmacy. The amount of active ingredient that can be combined with a carrier material to produce a single dosage form will vary depending upon the subject being treated and the particular mode of administration. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, in some embodiments from about 5 percent to about 70 percent, and in more specific embodiments from about 10 percent to about 30 percent. For example, compounds of the present disclosure can be formulated in a unit dose form between about 1 μg to 10 mg for treating pain. In some embodiments, compounds or compositions of the present disclosure can be formulated in a unit dose of about 1 μg to 20 μg, of about 20 μg to 1 mg, of about 1 mg to 10 mg, of about 10 mg to 100 mg, and of about 50 mg to 500 mg. In particular, an embodiment including a compound can be formulated in 0.1 μg, 0.2 μg, 0.5 μg, 1 μg, 20 μg, 50 μg, 100 μg, 200 μg, 500 μg, 1 mg, 2 mg, 5 mg, 10 mg, 20 mg, 50 mg, 100 mg, 200 mg, and 500 mg unit dose form.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions may be formulated for delivery via a catheter, stent, wire, or other intraluminal device. Delivery via such devices may be especially useful for delivery to the bladder, urethra, ureter, rectum, or intestine.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound of this invention, excipients such as lactose, talc, silicic acid, aluminum hydroxide, calcium silicates, and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers may also be used to increase the flux of the compound across the skin. The rate of such flux may be controlled by either providing a rate controlling membrane or dispersing the compound in a polymer matrix or gel.

Ophthalmic formulations, eye ointments, powders, solutions, and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and infrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

Methods of Treatment

As described above, aconitine is known to modulate the activity of sodium channels. Aconitine and its derivatives are therefore useful in treatments targeting such channels. Indeed, naturally occurring compounds from the *Aconitum* plant genus have been used for centuries in methods of treatment involving traditional Chinese medicine (TCM) (see Singhuber et al., *J. Ethnopharmacol.* 2009, 126, 18-30, and references therein, for a summary of the traditional uses, pharmacological targets and activities, and physical characterization of these agents). The use of traditional agents is hampered, however, by the high toxicity of many of the compounds found therein, by the inconsistent production and characterization of the natural agents, and by their ill-defined composition and potency. Rational design, synthesis, characterization, and testing of aconitine derivatives, according to the instant disclosure, thus provides advantageous compounds and compositions for use in methods of treatment for various conditions.

Thus, in another aspect of the invention, the subject compounds and pharmaceutical compositions thereof may be used in the treatment of a subject suffering from, for example, a voltage-gated sodium channel-enhanced ailment. Examples of voltage-gated sodium channel-enhanced ailments usefully treated according to the methods of the instant invention include acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, blepharospasm, cancer, cardiac arrythmia, epilepsy, focal dystonia, hyperhidrosis, muscle spasms, and urinary bladder relaxation.

The subject compounds and pharmaceutical compositions thereof are particularly useful in the treatment of a subject suffering from pain. Examples of pain that may be usefully treated according to the methods of the instant invention include acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, and pain from dysmenorrhea.

The subject compounds and pharmaceutical compositions thereof are additionally useful in the treatment of a subject, wherein the treatment reduces or eliminates wrinkles.

The compounds of the present disclosure and the pharmaceutical compositions comprising the same can be administered to a subject in one or more doses. In one embodiment, the compound or composition can be administered in an amount of about 1 μg to 10 mg per dose, e.g., about 1 μg to 5 μg, about 5 μg to 10 μg, about 10 μg to 50 μg, about 50 μg mg to 100 μg, about 100 μg to 200 μg, about 200 μg to 400 μg, about 400 μg to 800 μg, about 800 μg to 1 mg, about 1 mg to 2 mg, about 2 mg to 3 mg, about 3 mg to 4 mg, about 4 mg to 5 mg, about 5 mg to 6 mg, about 6 mg to 7 mg, about 7 mg to 8 mg, about 8 mg to 9 mg, or about 9 mg to 10 mg per dose.

In another embodiment, the amount of the compound or composition per dose is determined on a per body weight basis. For example, the amount of the compound or composition per dose, as determined on a per body weight basis, may be, for example, about 10 ng/kg, about 15 ng/kg, about 20 ng/kg, about 50 ng/kg, about 100 ng/kg, about 200 ng/kg, about 500 ng/kg, about 1 μg/kg, about 2 μg/kg, about 5 μg/kg, about 10 μg/kg, about 20 μg/kg, about 50 μg/kg, about 100 μg/kg, about 200 μg/kg, about 500 μg/kg, about 1 mg/kg, about 2 mg/kg, and about 5 mg/kg.

For example, in an embodiment, the compound or composition can be administered in an amount of about 15 ng/kg to 150 mg/kg, e.g., about 15 ng/kg to 30 ng/kg, about 30 ng/kg to 60 ng/kg, about 60 mg/kg to 120 ng/kg, about 120 ng/kg to 240 ng/kg, about 240 ng/kg to 480 ng/kg, about 480 ng/kg to 700 ng/kg, about 700 mg/kg to 1 μg/kg, about 1 mg/kg to 2 mg/kg, about 2 mg/kg to 4 mg/kg, about 4 mg/kg to 8 mg/kg, about 8 mg/kg to 15 mg/kg, about 15 mg/kg to 20 μg/kg, about 20 μg/kg to 30 mg/kg, about 30 μg/kg to 40 mg/kg, about 40 μg/kg to 60 μg/kg, about 60 mg/kg to 90 mg/kg, or about 90 μg/kg to 120 mg/kg, or more than about 120 μg/kg.

Those of skill will readily appreciate that dose levels can vary as a function of the specific compound or composition administered, the severity of the symptoms and the susceptibility of the subject to side effects. Preferred dosages for a given compound are readily determinable by those of skill in the art by a variety of means.

In an embodiment, multiple doses of the compound or composition are administered. The frequency of administration of the compound or composition can vary depending on any of a variety of factors, e.g., severity of the symptoms, and the like. For example, in an embodiment, the compound or composition is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in an embodiment, the compound or composition is administered continuously.

The duration of administration of the compound or composition, e.g., the period of time over which the compound or composition is administered, can vary, depending on any of a variety of factors, e.g., patient response, etc. For example, the compound or composition can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The methods of the instant invention are usefully employed in the treatment of any subject in which the instant compounds and compositions are effective. In particular, the methods of the invention are suited to the treatment of mammalian subjects, including, for example, farm and domestic animals, such as pets. The methods of treatment of the instant invention are particularly suited to the treatment of human subjects.

Methods of Preparing Aconitine Derivatives

In another aspect, the instant invention provides methods to prepare an aconitive derivative. As would be understood by one of ordinary skill in the art, such methods allow the production of structural derivatives that are useful in assessing structure-function relationships for a target molecule and that may provide additional novel therapeutic agents.

In one embodiment, the method of preparing an aconitine derivative comprises the step of selectively protecting an aconitine congener at the C-3 and C-13 hydroxyl groups. As would be understood by one of ordinary skill in the art, the selective protection of these hydroxyl groups facilitates the rational modification of functional groups at other locations within the protected aconitine congener molecule.

As used herein, the term "congener" refers to molecules having similar structure and function and that would thus be expected to have similar reactivities. Examples of naturally-occurring aconitine congeners include aconitine and mesaconitine, but other natural and synthetic molecules with structural similarity to aconitine should be understood to fall within the meaning of the term.

In some embodiments, the selective protection of the aconitine congener at the C-3 and C-13 hydroxyl groups is with a silyl group. In specific embodiments, the silyl group is a t-butyldimethylsilyl group or a trimethylsilyl group. In even more specific embodiments, the silyl group is a trimethylsilyl group.

In some embodiments of the invention, the method of preparing an aconitine derivative further comprises the step of selectively cleaving the C-14 ester of the protected aconitine congener. In specific embodiments, the selective cleavage is a reductive cleavage. In even more specific embodiments, the reductive cleavage is by diisobutylaluminum hydride.

According to some embodiments, the methods of the invention further comprise the step of selectively modifying the C-14 hydroxyl group of the cleaved protected aconitine congener. In preferred embodiments, the selective modification is an acylation.

Further Aspects

In yet another aspect, the invention provides novel compounds, compositions, and methods according to the following numbered paragraphs:

1. A compound represented by structural formula (I):

(I)

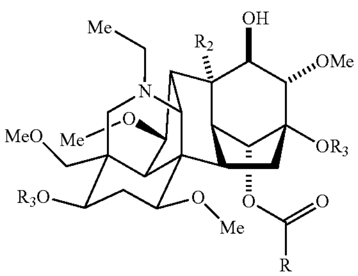

or a pharmaceutically acceptable salt or prodrug thereof, wherein:

R is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

$R_2$ is alkyl, alkoxy, or,

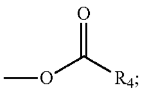

each $R_3$ is independently hydrogen or a protecting group;

each $R_4$ is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalkyl, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamindo, or azido;

provided that, when R is phenyl, $R_2$ is

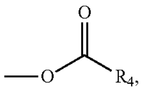

and each $R_3$ is hydrogen, then $R_4$ is not alkyl or alkenyl; and when R is p-methoxyphenyl, $R_2$ is

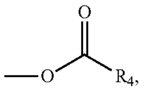

and each $R_3$ is hydrogen, then $R_4$ is not methyl.

2. The compound according to paragraph 1, wherein each $R_3$ is hydrogen.

3. The compound according to paragraph 1, wherein $R_2$ is

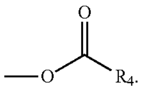

4. The compound according to paragraph 3, wherein $R_4$ is alkyl.

5. The compound according to paragraph 4, wherein $R_4$ is methyl.

6. The compound according to any one of paragraphs 1-5, wherein R is alkyl, aryl, or cycloalkyl, and is optionally substituted with 1 to 3 A groups.

7. The compound according to paragraph 6, wherein R is alkyl, phenyl, naphthyl, or cyclohexyl, and is optionally substituted with 1 to 3 A groups.

8. The compound according to paragraph 7, wherein the A groups are independently alkyl, alkoxyl, halo, trihalomethyl, or azido.

9. The compound according to any one of paragraphs 1-5, wherein R is selected from any one of the following:

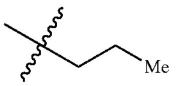

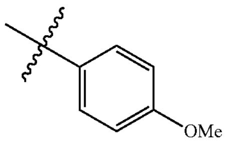

-continued

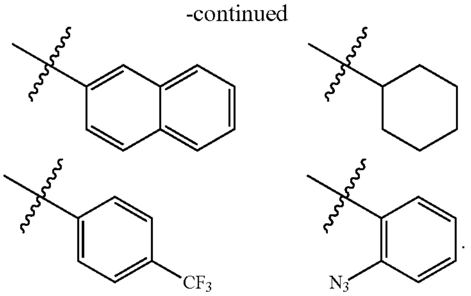

10. The compound of paragraph 9, wherein R is

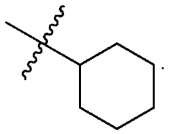 [SMILES: *C1CCCCC1]

11. The compound according to paragraph 1, wherein each $R_3$ is a protecting group.

12. The compound according to paragraph 11, wherein the protecting group is a silyl protecting group.

13. The compound according to paragraph 12, wherein the protecting group is t-butyldimethylsilyl or trimethylsilyl.

14. The compound according to paragraph 13, wherein the protecting group is trimethylsilyl.

15. The compound of any one of paragraphs 1-14, wherein the compound modulates the activity of a sodium channel.

16. The compound of paragraph 15, wherein the compound causes the sodium channel to open.

17. The compound of paragraph 16, wherein the compound causes the sodium channel to open at a lower membrane potential than aconitine.

18. The compound of paragraph 15, wherein the compound causes decreased flow of sodium through the sodium channel.

19. A pharmaceutical composition comprising the compound of any one of paragraphs 1-18 and a pharmaceutically acceptable carrier.

20. A packaged pharmaceutical comprising the pharmaceutical composition of paragraph 19 and instructions for using the composition to treat pain in a mammalian subject.

21. A method of treatment in a subject, comprising administering to the subject a compound of any one of paragraphs 1-18 in an amount effective to treat the subject.

22. The method of paragraph 21, wherein the treatment reduces neuronal activity in the subject or brings about muscular relaxation in the subject.

23. The method of paragraph 21, wherein the subject suffers from a voltage-gated sodium channel-enhanced ailment.

24. The method of paragraph 23, wherein the voltage-gated sodium channel-enhanced ailment is selected from the group consisting of: acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, blepharospasm, cancer, cardiac arrythmia, epilepsy, focal dystonia, hyperhidrosis, muscle spasms, and urinary bladder relaxation.

25. The method of paragraph 21, wherein the subject suffers from pain.

26. The method of paragraph 25, wherein the pain is acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, or pain from dysmenorrhea.

27. The method of paragraph 21, wherein the treatment reduces or eliminates wrinkles.

28. A method of preparing an aconitine derivative, comprising the step of:

i) selectively protecting aconitine at the C-3 and C-13 hydroxyl groups.

29. The method of paragraph 28, wherein the selective protection is with a silyl group.

30. The method of paragraph 29, wherein the silyl group is a t-butyldimethylsilyl group or a trimethylsilyl group.

31. The method of paragraph 30, wherein the silyl group is a trimethylsilyl group.

32. The method of paragraph 28, further comprising the step of selectively cleaving the protected aconitine at the C-14 position.

33. The method of paragraph 32, wherein the selective cleavage is a reductive cleavage.

34. The method of paragraph 33, wherein the reductive cleavage is by diisobutylaluminum hydride.

35. The method of paragraph 32, further comprising the step of selectively modifying the C-14 hydroxyl group.

36. The method of paragraph 35, wherein the selective modification is an acylation.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Semi-Synthetic Studies on Aconitine

Introduction

Aconitine and the related alkaloids batrachotoxin and grayanotoxin (see below) are potent neurotoxins that modify the electronic properties of voltage-gated sodium channels ($Na_V$) in excitable cells. Although these toxins are believed to act at a common receptor (site II) located in the intracellular region of the sodium channel (Catterall, *Neuron* 2000, 26, 13-25), each displays a unique pharmacological profile against $Na_V$ (Wang et al., *Cellular Signaling* 2003, 15, 151-159). Collectively, this class of toxins is known of elicit changes in activation potential (Rao et al., *Pflugers Arch—Eur. J. Physiol.* 2000, 439, 349-355), single channel conductance (Correa et al., *J. Gen. Physiol.* 1991, 97, 605-625), ion selectivity (Rao et al., *Pflugers Arch—Eur. J. Physiol.* 2000, 439, 349-355), and the rate of channel inactivation (Krueger et al., *Nature* 1983, 303, 172-174). The precise molecular details by which ligand binding affects these properties is largely unresolved. (Site-directed mutagenesis has been used to establish a subset of the residues comprising the batrachotoxin binding site, and a computational model has been developed. See Wang et al., *Molecular Pharmacology* 2006, 69, 788-795.)

Site II voltage-gated sodium channel modifiers.

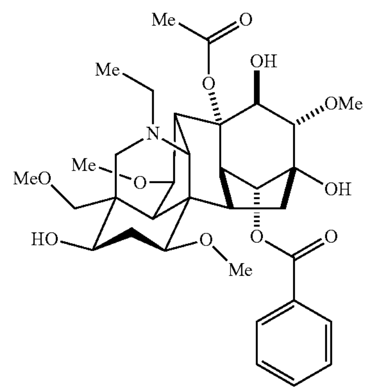

aconitine

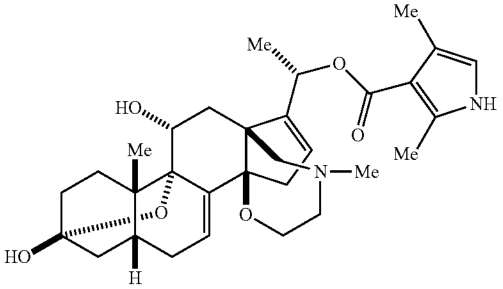

batrachotoxin

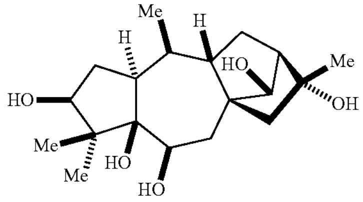

grayanotoxin

Aconitine is a member of the acanane family of diterpenoid alkaloids, which possess a common $C_{19}$ frame. Aconitine has long been known to display potent analgesic properties, however a narrow therapeutic window limits its potential as a medicinal agent (Tsuchida et al., *J. Urology* 2009, 181, 23-24, and references therein; Ameri, *Progress in Neurobiology* 1998, 56, 211-235). Binding of aconitine results in several important alterations in $Na_V$ function: (i) the potential at which $Na_V$ activates is shifted to more negative values; (ii) single channel conductance is decreased; (iii) selectivity for sodium over other cations is decreased; and (iv) the rate at which the channel inactivates is decreased or inhibited altogether. (These changes are known to depend both on the preparation of the protein of interest and on the isoform or isoforms present in the preparation. See Schmidt et al., *Pflügers Arch.* 1974, 349, 133-148; Mozhayeva et al., *Biochem. Biophys. Acta* 1977, 466, 461-473; Campbell et al., *J. Gen. Physiol.* 1982, 80, 713-731; Grishchenko et al., *Neuroscience* 1983, 9, 549-554): Aconitine binding is use-dependent—that is, high frequency stimulation of the channel results in much higher affinity of aconitine for $Na_V$, a result that is traditionally attributed to aconitine binding preferentially to the open state of the channel. Stabilization of this open state may account for the observed changes in activation potential in excitable cells modified by aconitine.

Computational models of the site II receptor of $Na_V$ have been developed based on mutagenesis studies, and by homology with crystallographically characterized $K^+$ ion channels, MthK (Jiang et al., *Nature* 2002, 417, 523-526) and KvAP (Jiang et al., *Nature* 2003, 423, 33-41), with which $Na_V$ is believed to share a common fold (for proposed alignments of these proteins, see Zhorov et al., *J. Neurochem.* 2004, 88, 782-799; Yamaguchi et al., *Mol. Pharmacol.* 2003, 64, 235-248; for computational model, see Tikhonov et al., *Ion Channels* 2005, 579, 4207-4212). While an allosteric mechanism of action has traditionally been suggested for these lipid soluble toxins, another possibility is a receptor location proximal to the channel pore, in which particular structural elements of each toxin physically occlude the channel pore, decreasing single channel conductance (Zhorov et al., *J. Neurochem.* 2004, 88, 782-799; Yamaguchi et al., *Mol. Pharmacol.* 2003, 64, 235-248). The precise location of the aconitine binding site on the sodium channel protein remains unknown, and no studies have yet addressed the mechanism(s) by which modification of the current-voltage relationship occurs by this toxin.

Acanane natural products have been subject to a number of semi-synthetic studies, including demethylation (Joshi et al., *J. Nat. Prod.* 1997, 60, 439-443, and references therein; Hardick et al., *Tetrahedron Lett.* 1994, 35, 3371-3374), deoxygenation (Mori et al., *Chem. Pharm. Bull.* 1991, 39, 2803-2806; Wada et al., *Chem. Pharm. Bull.* 1985, 33, 3658-3661), and ester hydrolysis (Katz et al., *Helv. Chim. Acta* 1984, 67, 2017-2022). The resulting natural product derivatives have been, in several cases, evaluated for biological activity, generally through mouse toxicity studies. Such data has helped to reveal the key pharmacological elements embedded in the toxin structure (Dzhakhangirov et al., *Chem. Nat. Compd.* 1997, 33, 190-202, and references therein; Mori et al., *Chem. Pharm. Bull.* 1991, 39, 379-383; Zhou et al., *Yaoxue Xuebao* 1984, 19, 641-646). The information content of these studies, however, is limited as toxicity can result, from the interaction of the modified ligand with any number of channel subtypes (or alternative protein targets) located in different tissues. Furthermore, toxicity can result from modification of a single electronic property of $Na_V$ (i.e. single channel conductance, current-voltage relationship, etc), or through any possible combination of these effects.

One objective of the studies described herein is to evaluate the importance of particular functional group moieties in aconitine on the biological activity of the toxin, and the specific influence of said groups on $Na_V$ modification. (Electrophysiological recordings demonstrating the effects of aconitine on a heterologously expressed sodium channel have been reported. See Rao et al., *Pflugers Arch—Eur. J. Physiol.* 2000, 439, 349-355.) The ability to measure electrophysiological recordings of a single sodium channel isoform expressed in a heterologous host (CHO cells) is an essential component of this work and allows us to accurately determine which physiological properties of the channel are affected upon toxin binding. An understanding of the interactions between aconitine derivatives and $Na_V$ provides an understanding of the structural elements that lead to the unique $Na_V$-modifying properties of aconitine and reveals intimate molecular details of the site II receptor in $Na_V$.

Semi-Synthetic Studies on Aconitine

The medicinal potential of aconitine has been recognized for centuries (Singhuber et al., *J. Ethnopharmacol.* 2009, 126, 18-30; lethal doses in humans have been estimated at 1-5 mg total dose, see Chan, *Clin. Toxicol.* 2009, 47, 279-285, and references therein), however, a narrow safety index has limited its use as a therapeutic agent. The desire to explore the pharmacological properties of aconitine has provided impetus for a number of semi-synthetic studies on aconitine. Preparations of the roots of the monkshood plant, from which aconitine is derived, that have been subjected to steaming or boiling water render these materials much less toxic; one of the products of this treatment has been characterized as des-benzoyl aconitine. It is speculated, therefore, that the benzoate of aconitine plays a pivotal role in ligand binding and $Na_V$ modification. With its characteristic effect on $Na_V$ gating, one possibility for how this structural element affects $Na_V$ function is through a cation-pi interaction between the aconitine C14 benzoate and the positively charged voltage sensor (Noda et al., *Nature* 1984, 312, 121-127) of $Na_V$. Aside from des-benzoyl aconitine, C14 substitutions on the natural product have not been described. The following section provides a synthetic pathway through which access to novel C14 esters is made possible.

Formal transesterification of the C14 benzoate of aconitine requires several selective transformations, as aconitine contains two ester functional groups; in addition, des-benzoyl aconitine contains three secondary and one tertiary hydroxyl units. Hydrolysis of aconitine under basic conditions (e.g. LiOH/THF) results in a complex mixture of products in which the acetate group is also cleaved, thus necessitating an alternative scheme for preparing the des-benzoyl derivative. Reductive conditions could potentially remove the C14 benzoate with some selectivity, as this moiety is somewhat more sterically accessible than the C8 acetate. Given our desire to replace the C14 benzoate with alternative ester functional groups, methods for protecting the C3, C13 and C15 alcohols were explored prior to attempts at C14 ester reduction. At 0° C., the combination of t-butyldimethylsilyltriflate (TBSOTf) and 2,6-lutidine allowed for selective protection of the secondary C3 and tertiary C13 alcohols. The secondary C15 alcohol was unreactive under these conditions, consistent with its sterically inaccessible location on the concave face of the C/D ring of the natural product.

Scheme 1. Selective TBS protection of C3 and C13 alcohols.

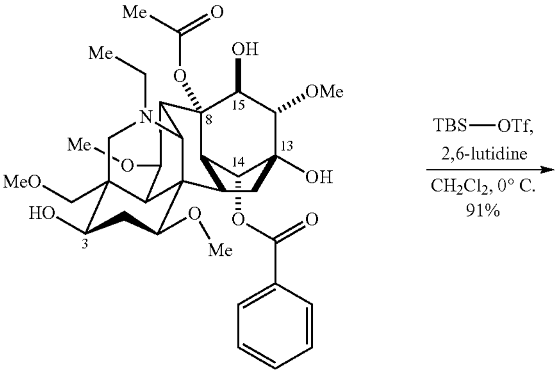

aconitine

-continued

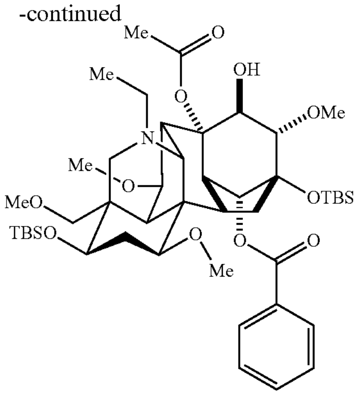

4.1

Several methods for cleaving the C14 benzoate of 4.1 were explored. Basic hydrolysis again led to complex product mixtures, which could not be assigned. By contrast, metal-hydride reductive conditions or strong-nucleophile addition gave a surprising result. Exposure of 4.1 to either DIBAL-H or EtMgBr left the C14 benzoate intact, giving instead selective removal of the C8 acetate to afford the corresponding C8-H and C8-Et derivatives, respectively. This type of substitution reaction has been reported for cases in which alcohols and carboxylic acids act as nucleophiles. The perfect antiperiplanar alignment of the nitrogen lone pair, C17-C7 and C8-OAc bonds renders the acetate group susceptible to Grob-type fragmentation (Pelletier et al., *J. Nat. Prod.* 1992, 55, 1-24). In fact, methanol was found to displace the C8 acetate in good yield at reflux without the need for any additional acid catalyst or promoter.

Scheme 2. C8 acetate is labile due to antiperiplanar alignment of the nitrogen lone pair, C17-C7 and C8-OAc bonds.

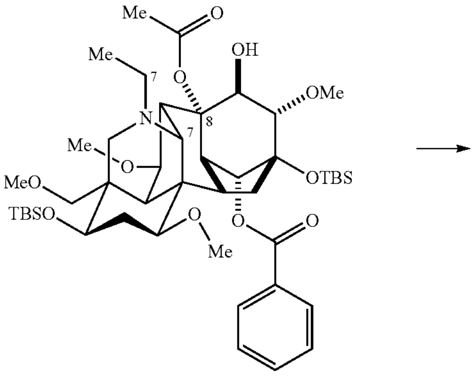

4.1

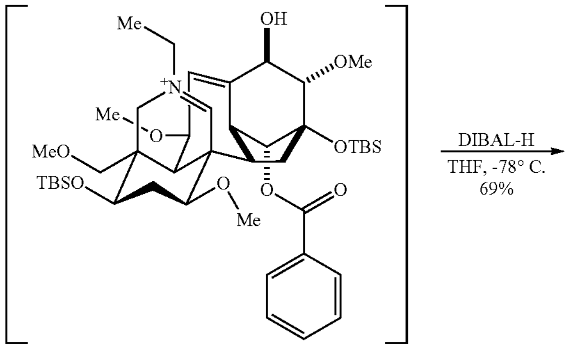

-continued

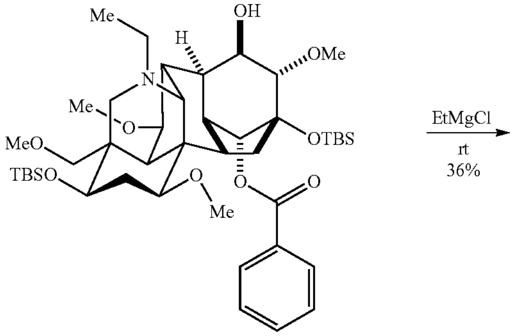

4.2

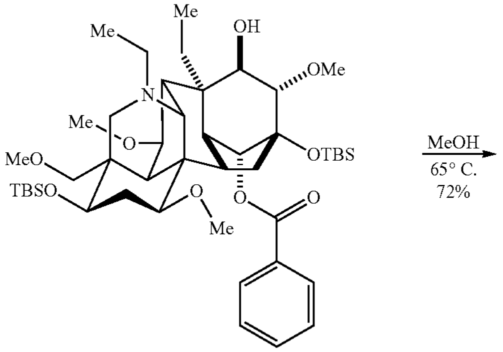

4.3

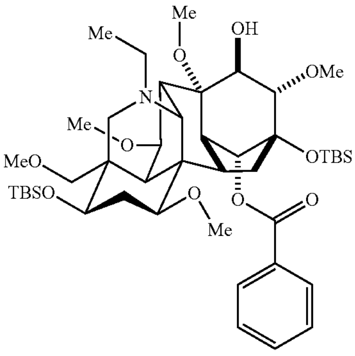

4.4

The robustness of the C14 benzoate in 4.1 indicated that the C13 TBS protecting group might block nucleophilic attack at the adjacent carbonyl. As a testament to the sterically crowded environment around C13 and C14, exposure of 4.1 to a variety of fluoride sources (e.g. tetra-n-butylammonium fluoride (TBAF), HF.pyridine) failed to cleave the C13 TBS protecting group. To overcome both the challenge of cleaving the C14 benzoate and to avoid a difficult deprotection later in the synthesis, a less sterically demanding protecting group was chosen. Although the product proved somewhat harder to handle, as it was quite sensitive to mild Brønsted and Lewis acids (e.g., silica gel) (warming the reaction of 1 and TMSCl to room temperature afforded the C3, C13 and C15 tri-silylated product. The protecting group at C15, however, proved quite difficult to remove under $F^-$ deprotection conditions), both the C13 and C3 alcohols could be cleanly and efficiently silylated at 0° C. using trimethylsilyl chloride (TMSCl) with $Et_3N$. Exposure of this protected material to TBAF smoothly returned aconitine.

Scheme 3. Conditions for selective protection of C3 and C13 alcohols of aconitine.

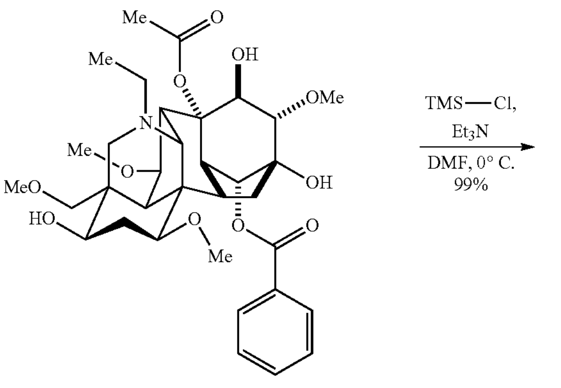

aconitine

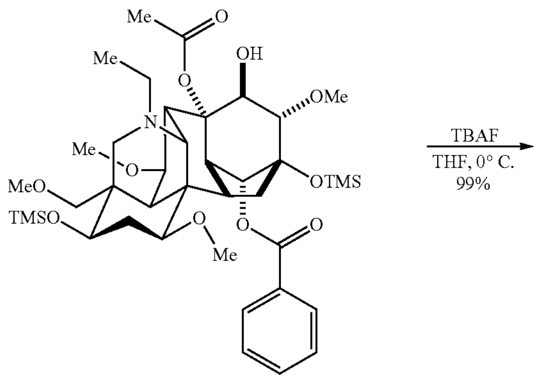

4.5 aconitine

With a less sterically demanding C13 protecting group in place, conditions for cleavage of the C14 benzoate were again screened. This time, low temperature DIBAL-H reduction using toluene as solvent proved effective for selective cleavage of the C14 benzoate. Under these conditions, the C8 acetate was unreactive, and good yields of the desired product were obtained. Esterification of the resulting secondary alcohol proved somewhat challenging as standard carboxylic acid activation conditions (CDI, EDCI, $(COCl)_2$) promoted cleavage of the C3 silyl protecting group and esterification of the resulting secondary alcohol. However under strictly anionic conditions, which involved deprotonation of the C14 alcohol with lithium hexamethyldisilazane (LHMDS), the C14 secondary alcohol reacted efficiently with preformed acid chlorides, furnishing the desired esters. As expected, silyl deprotection with tetra-n-butylammonium fluoride (TBAF) was generally high yielding; electron-withdrawing esters, however, proved particularly labile under these conditions, a property that could not be mitigated by using acetic acid-buffered conditions.

Scheme 4. A three-step transesterification of C14 alcohol.

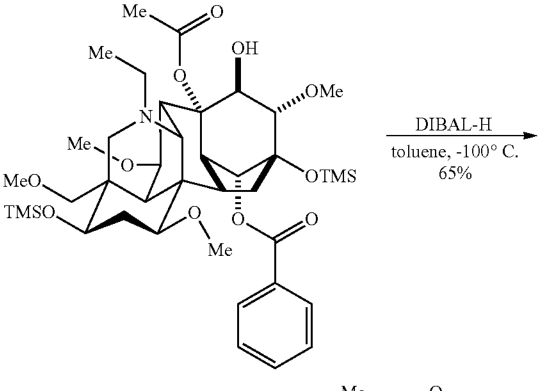

4.5

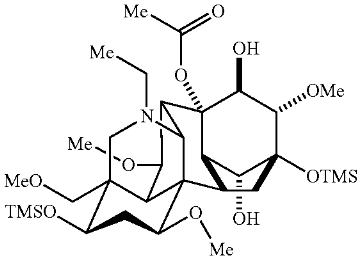

4.6

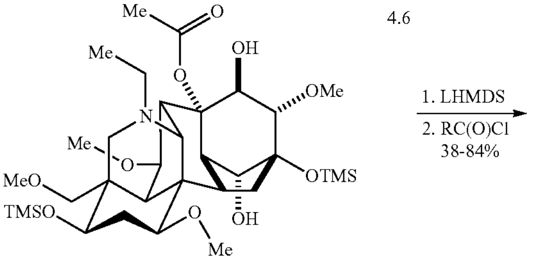

4.6

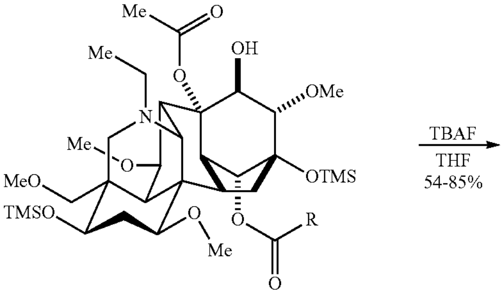

4.7

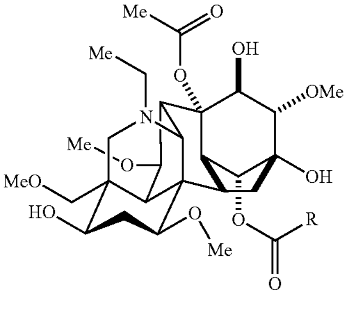

4.8

Several ester derivatives of aconitine with varying steric and electronic properties were prepared. To ascertain whether a cation-pi interaction is responsible for the shift in activation threshold observed on aconitine binding, a cyclohexyl variant 4.8d was synthesized. Similarly, a straight-chain n-butanoate ester, 4.8a, was prepared. Electron donating (4-methoxy, 4.8b) and electron withdrawing (4-trifluoromethyl, 4.8e) benzoates were assembled, along with the naphthoate structure 4.8c. Finally, azidobenzoate 4.8f was synthesized as a potential photoaffinity label. (An analogous azidobenzoate derivative of batrachotoxin has been used for photoaffinity labeling of $Na_V$. See Trainer et al., *J. Biol. Chem.* 1996, 271, 11261-11267.)

Replacements for C14 benzoate designed to probe the ligand-receptor interactions responsible for shift of current-voltage relationship and partial channel block.

4.8

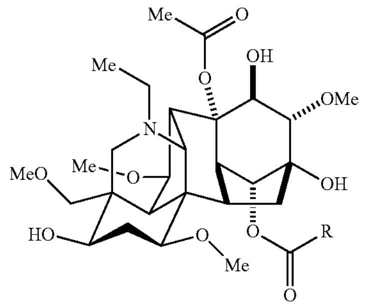

R =

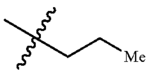

4.8a

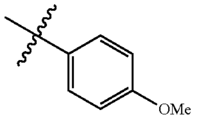

4.8b

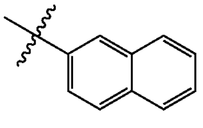

4.8c

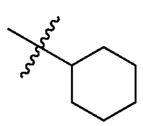

4.8d

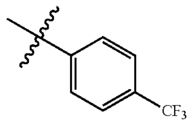

4.8e

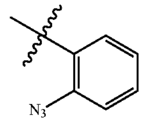

4.8f

Establishment of the Effect of Aconitine on Modification of $Na_V$ and the Degree to which Modification is Reversible Binding of aconitine to $Na_V$ is use-dependent and is known to result both in a left shift of the current-voltage (I-V) relationship and in partial block of the channel. Interestingly, one facet of aconitine binding that has not been addressed is the degree to which aconitine binding is reversible. To determine whether aconitine binding is reversible, two experiments were designed. First, as block by aconitine is known to be use dependent, peak current was measured as a function of pulse number in the presence of two different concentrations of aconitine. Since aconitine binds preferentially to the open state of the sodium channel, a pulse train was applied sequentially with a control pulse used to record peak current. The pulse train consisted of a series of 50 depolarizing pulses (from −100 mV holding potential to 0 mV, 10 ms duration) applied at 10 Hz frequency, while the control pulse consisted of a single depolarizing pulse (from −100 mV holding potential to 0 mV test potential, 10 ms duration).

Pulse trains of 10 Hz frequency and control pulses were applied sequentially to cells expressing $rNa_V1.4$, and currents elicited from the control pulse were recorded after each pulse train. This process was repeated until the current elicited from the control pulse had reached a steady state and was no longer decreasing with each additional pulse train. If block were irreversible, this steady state current would be expected to be independent of toxin concentration—the toxin would not be able to dissociate from its receptor, and the number of toxin molecules is much greater than the number of sodium channels (assuming a 100 μL chamber containing 1000 CHO cells, each expressing 10,000 sodium channels, at 50 μM concentration toxin molecules outnumber receptors by a factor of $3\times10^8$:1), therefore, all receptors would eventually reach the bound state.

Figure 9:
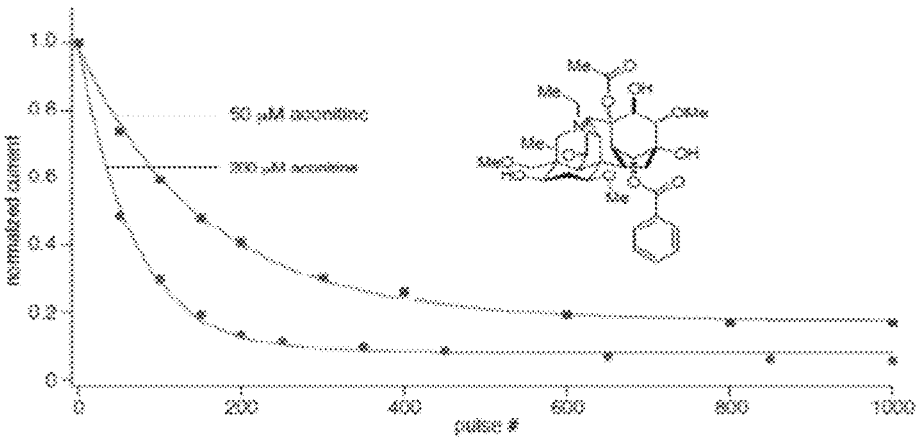
FIG. 9. Current vs. pulse number after perfusion of 50 μM or 200 μM aconitine.

FIG. 9 shows a series of whole cell current traces elicited from Chinese hamster ovary (CHO) cells expressing $rNa_V1.4$, plotted as a function of pulse number, in the presence of 50 μM aconitine and 200 μM aconitine. In the presence of 50 μM aconitine, approximately 800 depolarizing pulses are required to reach a steady state, and 83% of peak current is blocked. However, in the presence of 200 μM aconitine, only 300 depolarizing pulses are required to reach a steady state in which approximately 94% of peak current is blocked. While a difference in the effective rate for achieving steady state is to be expected, the differential degree of block upon reaching steady state indicates that at the 50 μM concentration, fewer sodium channels are in the toxin-bound state. These data indicate that an equilibrium, whose position depends on toxin concentration, has been reached, and therefore aconitine binding must be reversible (batrachatoxin binding has also been shown to be fully reversible. See Catterall, *J. Biol. Chem.* 1975, 250, 4053-4059).

Figure 10:
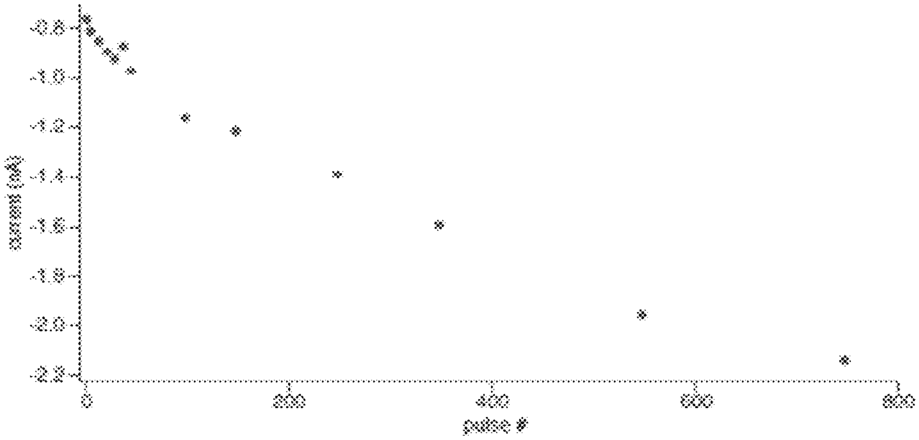
FIG. 10. Dissociation of aconitine from the sodium channel.

In a second experiment, after reaching a steady state (a solution of 200 μM aconitine was applied, followed by 1000 depolarizing pulses), buffer containing no toxin was applied to the cell and peak current was again measured as a function of pulse number. FIG. 10 shows that peak current increases as a function of pulse number, therefore aconitine must be dissociating from $Na_V$ over the course of the experiment. Because of the large number of pulses required to reach a steady state, both after application of aconitine and during wash off, full current restoration was difficult to achieve experimentally, however, significant current restoration is clearly observed. It is noteworthy that little or no increase in current was observed during wash off when no depolarizing pulses were applied and peak current was measured as a function of time. These results indicate that aconitine dissociates preferentially from the open state of the channel (Wang et al., *Cellular Signalling* 2003, 15, 151-159).

Electrophysiology Recordings of $Na_V$ Modified by Aconitine C14 Cyclohexanoate

Aconitine partially blocks $Na_V$ conductance and shifts the current-voltage (I-V) relationship in the hyperpolarizing direction. The manner in which aconitine exhibits these effects and the specific functional groups that contribute both to block and I-V shift have not been established. One possible explanation for this observed phenomenon is that the C14 benzoate of aconitine contacts the $Na_V$ voltage sensor, and that a pi-cation interaction between this aromatic moiety and the positively charged voltage sensor contributes to I-V modification. To test this theory, an aconitine derivative was synthesized in which the C14 benzoate was replaced by a cyclohexanoate, yielding an aconitine derivative with similar molecular dimensions but absent the aromatic moiety that might engage in a pi-cation interaction.

A non-aromatic benzoate isostere of aconitine.

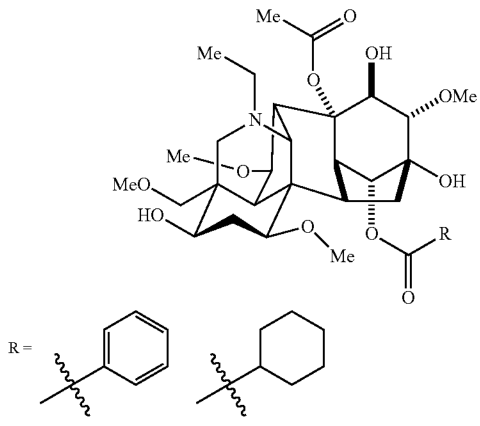

aconitine 4.8d

Figure 11:
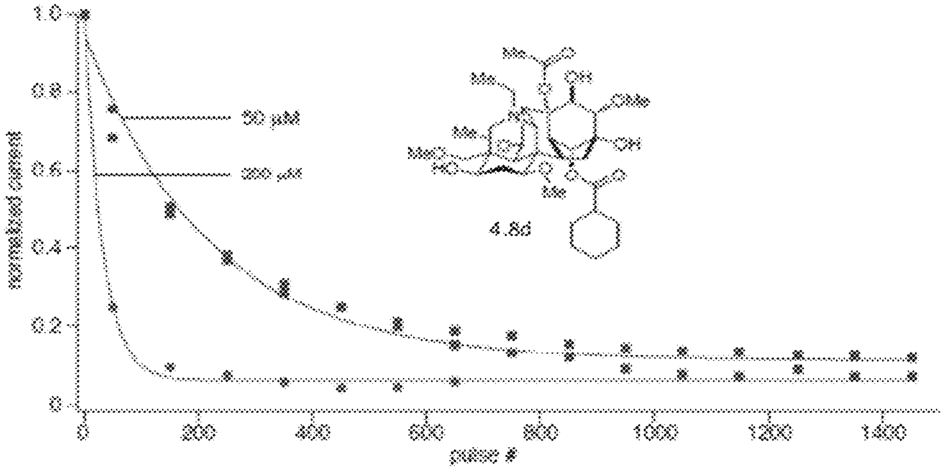
FIG. 11. Current vs. pulse number for acontine C-14-cyclohexanoate 4.8d.

To determine the effect on channel block and I-V relationship, whole cell currents were recorded in cells expressing $Na_V$ in the presence of cyclohexanoate 4.8d. FIG. 11 shows a plot of peak current vs. pulse number after a 50 μM and 200 μM solution of 4.8d was applied. When 200 μM 4.8d was applied, a steady state current was reached after just 200 pulses, resulting in block of 94% of peak current. The data are fit to a single exponential. In the case of 50 μM 4.8d, two experiments are plotted, with a curve fit to the average of the two. Approximately 1000 pulses were required to reach a steady state, with 90% of peak current blocked. This degree of block is slightly greater than is seen with the same concentration of aconitine.

Figure 12:
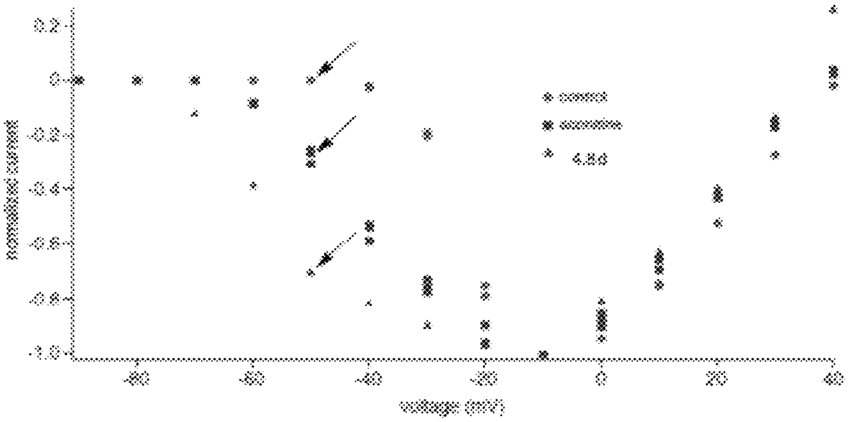
FIG. 12. Current-voltage curves for control channels and those modified by aconitine and 4.8d. Arrows show recorded currents at −50 mV.

To determine if the shift in I-V relationship is affected by the aromaticity of the aconitine C14 benzoate, current-voltage relationships were recorded for control cells expressing $Na_V$, those that had been modified by aconitine, and those that had been modified by aconitine C14-cyclohexanoate 4.8d. For the modified channels, solutions of 50 μM concentration of the respective toxins were perfused onto the cells, and then depolarizing pulses were applied until a steady state current was observed, generally requiring about 1000 pulses. At that time, current-voltage relationships were again recorded. FIG. 12 shows recordings derived from channels modified by both toxins, overlaying a control cell. A shift towards hyperpolarizing potentials is clearly observed in both cases. Currents recorded at −50 mV are highlighted for all three experiments. In control cells, no current was observed at this potential, while those modified by aconitine and the corresponding cyclohexanoate derivative 4.8d passed substantial currents, indicating that channels modified by these toxins open more readily at lower membrane potentials. In fact, cyclohexanoate 4.8d has a more pronounced effect in this respect than the natural product. In any case, the data indicate that a cation-pi interaction is likely not responsible for the observed I-V modification of $Na_V$.

In summary, aconitine binds to the voltage-gated sodium channel ($rNa_V$ 1.4) in a reversible, use-dependent manner, decreasing the channel's ability to pass current and shifting the current-voltage relationship in a hyperpolarizing direction. The precise structural elements of the toxin responsible for each of these effects remains unclear, however, and without intending to be bound by theory, a cation-pi interaction between the C14 benzoate of aconitine and the voltage sensor moiety does not appear to be a requisite interaction. The selective chemistries presented herein make possible the construction of other aconitine derivatives that provide further insight into the precise molecular architecture of the aconitine binding site and the ability of aconitine derivatives to alter channel function.

Effect of Aconitine Derivatives on $Na_V$ Channel Conductance

Aconitine partially blocks $Na_V$ conductance and shifts the current-voltage (I-V) relationship in the hyperpolarizing direction. The manner in which aconitine exhibits these effects and the specific functional groups that contribute both to block and I-V shift have not been established. One possible explanation for this observed phenomenon is that the aromatic moiety of the C14 benzoate of aconitine participates in a pi-cation interaction with a positively charged residue in the inner pore of the NaV channel. To test this theory, aconitine derivatives were synthesized in which the C14 benzoate was replaced by ester of varying bulk and polarity. A series of electrophysiological experiments were conducted to evaluate the effects of aconitine and selected C14 derivatives with $rNa_V$1.4 channel expressed heterologously in Chinese hamster ovary (CHO) cells.

Structure and Nomenclature of Aconitine Derivatives:

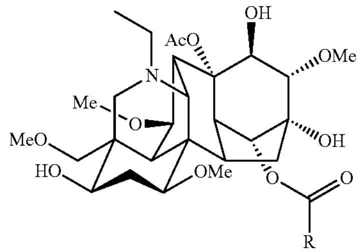

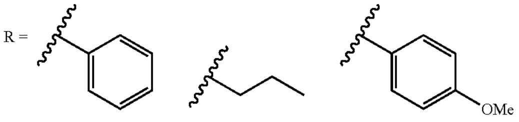

aconitine 4.8a 4.8b

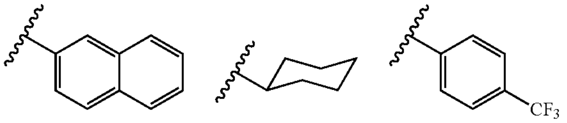

4.8c 4.8d 4.8e

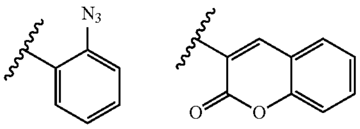

4.8f 4.8g

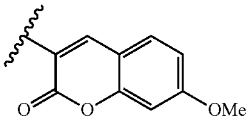

4.8h

Structure 1: Aconitine
Structure 4.8a: ACO-butanoate
Structure 4.8b: ACO-4′-methoxybenzoate; ACO-4′-MeO-benzoate
Structure 4.8c: ACO-2′-naphthoate; Naphth-ACO
Structure 4.8d: ACO-cyclohexanoate; Cyclohex-ACO
Structure 4.8e: ACO-4′-trifluoromethylbenzoate; ACO-4′-$CF_3$-benzoate
Structure 4.8f: ACO-2′-azidobenzoate
Structure 4.8g: ACO-3′-acylcoumarin; Coumaryl-ACO
Structure 4.8h: ACO-3′-acyl-7′-methoxycoumarin; MeO-coumarin-ACO Use-Dependence of Aconitine Derivatives Block by aconitine is known to be use-dependent, therefore the use-dependence of the C14 derivatives of aconitine was evaluated. Peak Na current was measured as a function of pulse number in the presence of different concentrations of the molecules. All the molecules tested displayed a pulse dependence in whole-cell patch-clamp experiments. Since aconitine binds preferentially to the open state of the sodium channel, a pulse train was applied sequentially with a control pulse used to record peak current. The pulse train consisted of a series of 50 depolarizing pulses (from −100 mV holding potential to 0 mV, 10 ms duration) applied at 10 Hz frequency, while the control pulse consisted of a single depolarizing pulse (from −100 mV holding potential to 0 mV test potential, 10 ms duration).

Pulse trains of 10 Hz frequency and control pulses were applied sequentially to CHO cells expressing rNaV1.4, and currents elicited from the control pulse were recorded after each pulse train. This process was repeated until the current elicited from the control pulse had reached a steady state and was no longer decreasing with each additional pulse train. If block were irreversible, this steady state current would be expected to be independent of toxin concentration—the toxin would not be able to dissociate from its receptor, and the number of toxin molecules is much greater than the number of sodium channels, therefore, all receptors would eventually reach the bound state.

Figure 13:
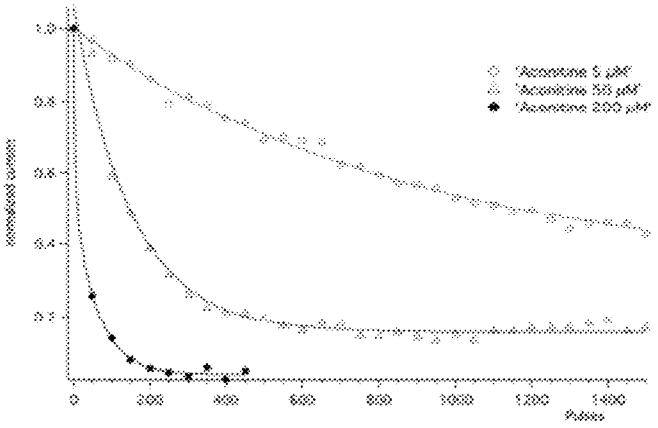
FIG. 13. Pulse dependence of aconitine at different concentrations. Peak $Na^+$ currents elicited from CHO cells expressing r$Na_V$1.4, plotted as a function of pulse number, in the presence of 5, 50 and 200 μM aconitine.

FIG. 13 shows a series of whole cell current traces elicited from CHO cells expressing rNaV1.4, plotted as a function of pulse number, in the presence of 5, 50 and 200 μM aconitine. In the presence of 50 μM aconitine, approximately 800 depolarizing pulses are required to reach a steady state, and 83% of peak current is blocked. However, in the presence of 200 μM aconitine, only 300 depolarizing pulses are required to reach a steady state in which approximately 94% of peak current is blocked. In contrast, at lower concentration such as 5 the steady-state block reaches 40% after over 2500 pulses. While a difference in the effective rate for achieving steady state is to be expected, the differential degree of block upon reaching steady state suggests that at the 50 concentration, fewer sodium channels are in the toxin-bound state. These data indicate that an equilibrium, whose position depends on toxin concentration, has been reached, and therefore aconitine binding must be reversible.

Figure 14:
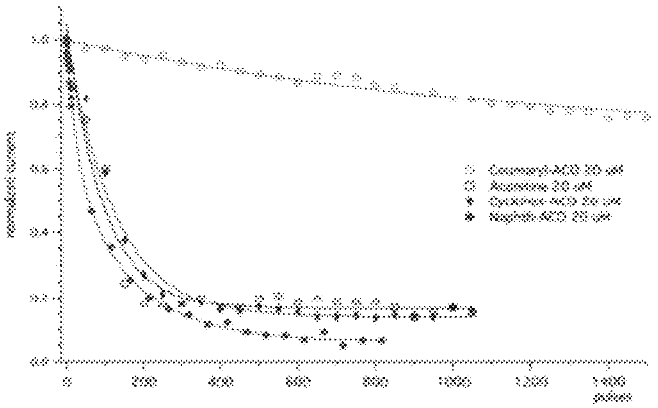
FIG. 14. Pulse-dependence of channel block by aconitine, 4.8c, 4.8d, and 4.8 g at 20 μM; whole-cell patch clamp configuration with r$Na_V$1.4 in CHO cells.
Figure 15:
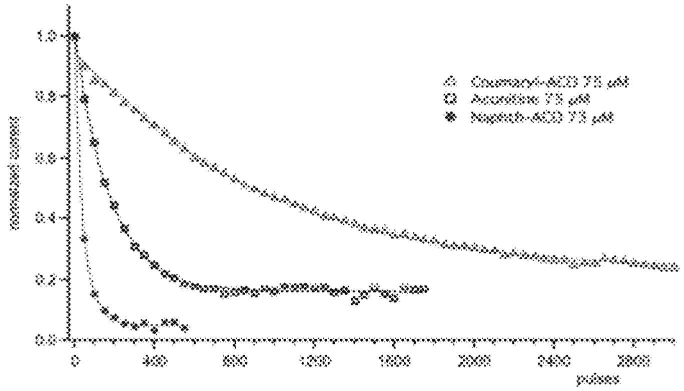
FIG. 15. Pulse-dependence of channel block of aconitine, 4.8c and 4.8 g at 75 μM; whole-cell patch clamp configuration with r$Na_V$1.4 in CHO cells.

The nature of the C14-ester influences the rate at which steady-state $Na^+$ current block is attained. Naphth-ACO (4.8c) showed the highest kinetics of attaining maximum $Na^+$ current block (FIGS. 14 and 15). At a concentration of 20 μM, aconitine and ACO-cyclohexanoate (4.8d) display a similar rate of current reduction to reach a steady-state block after around 600 pulses (81% and 85% block, respectively). The rate of current block of Na current with 20 μM ACO-naphthoate (4.8c) was slightly faster than aconitine and 4.8d, and stabilized at around 95% block after 800 pulses. In contrast, Coumaryl-ACO (4.8 g) showed a much slower rate and blocked only 21% current after over 2500 pulses. At higher concentrations, the difference in pulse-dependence of the aconitine derivatives was more evident. For example, FIG. 15 shows peak $Na^+$ current elicited plotted as a function of pulse number, in the presence of 75 μM aconitine and coumaryl-ACO (4.8 g), and 73 μM naphth-ACO (4.8c). Naphth-ACO (4.8c) almost blocked over 97% of NaV1.4 within 300 pulses, whereas the natural product aconitine required 800 pulses and blocked only 87% of Na current. Coumaryl-ACO was also showed the slowest molecules to reach a steady-state block; with 77% block after over 3000 pulses. Of all the compounds tested, naphth-ACO (4.8c) displayed the most favorable kinetics of binding $Na_V$ channels.

$Na^+$ Current Block

The ability of the synthesized aconitine derivatives to block $Na_V$ channels was evaluated with patch-clamp experiments in the whole-cell configuration on CHO cells expressing $rNa_V1.4$ heterologously. A buffer solution containing the toxin was applied to the cells, whole-cell $Na^+$ currents were recorded until the decreasing current reached a steady-state (300 to 3000 pulses, depending on the molecules and concentrations). The peak $Na^+$ currents were measured with a depolarizing test pulse (from −100 mV holding potential to 0 mV test potential, 10 ms duration).

The aconitine derivatives partially blocked $Na^+$ currents in a dose-dependent manner. The activity of selected aconitine derivatives is summarized in Table 2 as the percentage of current that remained after reaching a steady-state level for a given concentration of toxin. The most potent channel blocker was the naphthoate derivative 4.8c, which nearly completely blocked all Na current at concentrations of 20 μM and above (≤5% current was observed). The current block observed with 21 μM ACO-cyclohexanoate (4.8d) at is similar to that of 20 μM aconitine (15% and 19% block, respectively). The presence of a ortho-azido group on the benzoate ester (4.8f) showed a slightly reduced blocking effect compared to aconitine: 22% current remained with 50 μM 4.8f versus 15% current with aconitine. Interestingly, the presence of a rather large ester group such as a coumarin 4.8 g still displayed partial current block, however with much reduced efficiency: it required 75 μM to achieved the current levels observed with 20 μM aconitine. These results demonstrate that (i) the C14-ester can be modified and still retain current block activity, and (ii) the current block effect of aconitine can be modulated according to the nature of the ester.

TABLE 2

Effect of selected molecules on $Na^+$ currents $rNa_v1.4$ channels expressed in CHO cells.

| | | % Remaining current after reaching steady-state binding[a] | | | | |
|---|---|---|---|---|---|---|
| | | 5 μM | 20 μM | 50 μM | 75 μM | 200 μM |
| Aconitine | 1 | 40 | 19 | 13 | 13 | 5 |
| ACO-cyclohexanoate | 4.8d | 82 | 15[b] | 10 | — | 6 |
| ACO-2'-naphthoate | 4.8c | 38 | 5 | — | 3[c] | 3 |
| ACO-2'-azidobenzoate | 4.8f | — | — | 22 | — | — |
| ACO-3'-acylcoumarin | 4.8g | — | 79 | — | 23 | — |

[a]Values represent averages of two or more assays.
[b]Concentration was 21 μM.
[c]Concentration was 73 μM.

Binding Reversibility

The degree to which aconitine derivatives binding is reversible was assessed by perfusing buffer solution that did not contain the toxin immediately following the experiments that assayed for current block. Since the molecules bind to the open-state of the Nav channel their release also requires activation pulses. In typical experiments, buffered external solution was perfused and a pulse train sequence was applied to the patch-clamp until the current reached a steady-state for at least two minutes.

Table 3 summarizes these wash-off experiments with four representative molecules. In general, the toxins all showed some degree of irreversibility. As a reference, $Na^+$ current is reduced to 13% with 75 μM of the natural product aconitine and only returns to 62% after wash-off; whereas it returns to 94% after wash-off at 20 μM. The cyclohexanoate analog 4.8d only restored 79% current after wash-off at 20 μM. The two derivatives bearing large aromatic esters, 4.8c and 4.8 g, did not restore substantial current. Of all the analogs evaluated, the naphthoate 4.8c proved to be completely irreversible, irrespective of the concentration used.

TABLE 3

Reversibility of selected molecules upon wash-off experiments.[a]

| | | Current measured at 75 μM (%) | Current after wash-off (%) | Current measured at 20 μM (%) | Current after wash-off (%) |
|---|---|---|---|---|---|
| Aconitine | 1 | 13 | 62 | 19 | 94 |
| ACO-cyclohexanoate | 4.8d | — | — | 15[c] | 79[c] |
| ACO-2'-naphthoate | 4.8c | 3[b] | 3[b] | 3 | 4 |
| ACO-3'-acylcoumarin | 4.8g | 23 | 31 | 79 | 83 |

[a]Values represent averages of two or more assays.
[b]Concentration was 73 μM.
[c]Concentration was 21 μM.

Conclusions

A range of aconitine analogs were shown to modify the conductance of $Na_V$ channels. The variability in the effect observed with different derivatives demonstrates that the C14 ester plays an important role in the interaction between the toxins and the $Na_V$ channel protein. The fact that the properties of cyclohexanoate 4.8d were very similar to aconitine itself makes it unlikely that the activity of aconitine is tied to its aromatic moiety engaging in a pi-cation interaction. The naphthoate analog 4.8c exemplifies a C14 aconitine ester derivative having improved properties over the natural product aconitine. For instance, a molecule such as 4.8c achieves steady-state channel block faster than aconitine, it is a more potent $Na_V$ channel blocker than aconitine, and binds irreversibly to $Na_V$ channels.

Modification of the Current-Voltage Relationship

In addition to partially blocking the channel, binding of aconitine to $Na_V$ also causes a shift in the thresholds of both activation and inactivation of the $Na_V$ channels. The effect of the aconitine analogs on these properties was evaluated by measuring current-voltage (I-V) relationships with electrophysiology recordings.

Modification of the Activation Threshold

To determine the effect on current-voltage (I-V) relationship of the aconitine derivatives, whole cell currents were recorded in cells expressing $Na_V$ in the presence of aconitine derivatives. Control I-V plots were recorded with unmodified $Na_V$1.4, to which were compared $Na_V$ channels modified by aconitine as well as by selected analogs. For the modified channels, solutions of the respective toxins were perfused onto the cells, and then depolarizing pulses were applied until a steady state current was observed, generally requiring about 1000 pulses. A sequence of test pulses was then recorded to determine the current-voltage relationships (using a step protocol in which CHO cells were depolarized for 10 ms from a holding potential of −100 mV to a range of potentials from −95 mV to +30 mV in 5 or 10 mV increments; peak currents were normalized to the maximum peak current and plotted against voltage).

Figure 16:
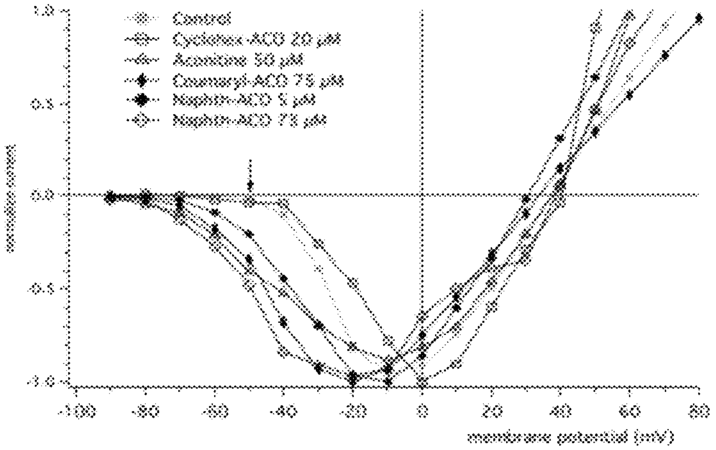
FIG. 16. Effect of selected compounds on the current-voltage relationship of r$Na_V$1.4 expressed in CHO cells. The arrow points to −50 mV, the normal activation threshold of r$Na_V$1.4.

All aconitine derivatives modified the potential at which the $Na_V$ channel gets activated. FIG. 16 shows selected recordings derived from channels modified by toxins, overlaid with a control cell (light gray). A shift towards hyperpolarizing potentials is clearly observed in most cases. The arrow in FIG. 16 indicates the −50 mV threshold at which unmodified rNaV1.4 channels typically get activated; in control cells, no current is observed at this membrane potential. In contrast, when the $Na_V$ are bound to aconitine derivatives, substantial current is observed (20% to 55%). The I-V relationship plots also reveal the membrane potential at which maximum inward Na current occurs. In unmodified rNav1.4, maximum current is observed at around −10 mV; similarly, 50 μM aconitine also reaches highest $Na^+$ current close to the same potential. Most C14-analogs of aconitine show a maximum current at lower potential. For instance, both ACO-coumarin (4.8 g) and ACO-naphthoate (4.8c) shift this potential towards hyperpolarized by as much as 10 mV when applied at 75 μM. In fact, both 4.8c and 4.8 g appear to have a more pronounced effect in this respect than the natural product as they cause an larger current density at any given potential than the natural product. In contrast, for 20 μM cyclohexyl-ACO (4.8d), maximum current is observed at 0 mV—a 10 mV hypopolarized shift.

Figure 17:
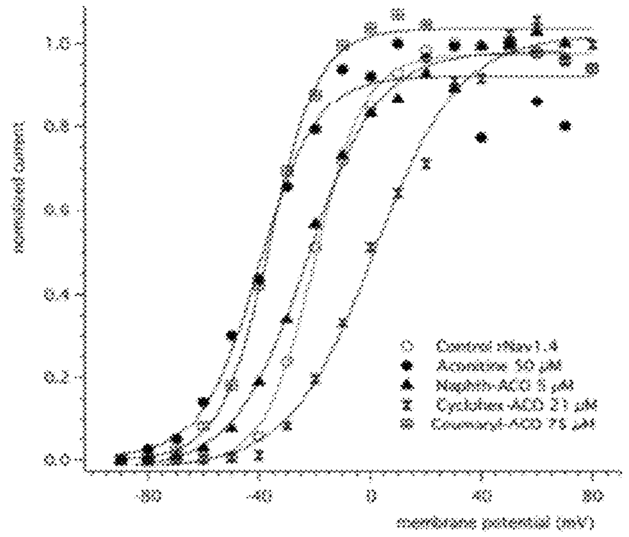
FIG. 17. Conductance-voltage relations for r$Na_V$1.4 in the presence of aconitine analogs. Activation parameters ($V_{0.5}$) are shown in Table 4.

The conductance-voltage relation (G-V) curves for rNav1.4 in the presence of aconitine derivatives is shown in FIG. 17 (activation parameters are listed in Table 4). The G-V curves for rNav1.4 exhibit negative shifts in the voltage for half activation ($V_{0.5}$) for most of the aconitine analogs tested. For example, 4.8c, 4.8d, and 4.8 g induced a 3 mV to 20 mV shift in the threshold of activation for rNav 1.4 (concentrations 5 μM to 75 μM). The effects of the coumarinyl 4.8 g on channel activation resembled that of aconitine. Interestingly certain compounds such as cyclohexyl-ACO 4.8d shifted the voltage of half-activation ($V_{0.5}$) by more than 20 mV towards the hypo-polarization. To our knowledge, this the first time that a small molecule is shown to increase the threshold of activation and provides a novel approach for treating conditions where a dysfunction of the NaV channels causes repeated/spontaneous firing (e.g., hyperalgesia).

The molecules tested behave as activators; when bound to NaV channels, they increase their probability of opening at the resting potential of the membrane, thereby possibly triggering repeated spontaneous firing of action potentials. Interestingly, whereas 20 μM cyclohexyl-ACO (4.8d) did not significantly shift the activation threshold of the channels, it shifted the threshold for inactivation towards higher potentials.

Modification of Steady-State Inactivation

Binding of aconitine is also known to cause NaV channels to inactivate at lower membrane potentials than the their natural state. The exact structural causes for this perturbation of the channels is still unknown. Given that the modified C14-esters of aconitine prepared influenced the activation properties of the channels, we investigated whether variation of the steric bulk and/or electronic properties of the C14-ester moiety had an effect on steady-state inactivation of Nav channels. Steady-state inactivation gives a measure of the rate at which NaV channels transition from the open state (where $Na^+$ ions flow through the pore) to the inactivated state, where the channel prevents $Na^+$ ions flow without having undergone the full conformational change leading the closed state.

Figure 18:
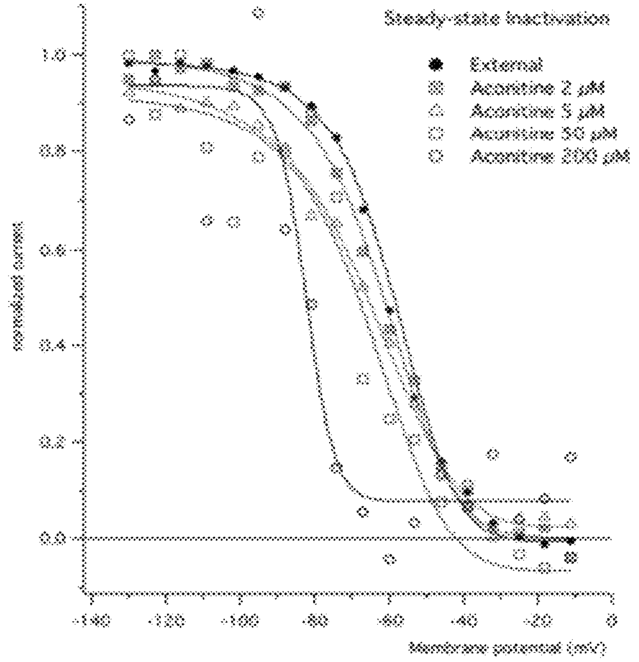
FIG. 18. Normalized steady-state inactivation of $Na_V$1.4 channels before (filled symbols) and after (open symbols) channel modification by aconitine.

FIG. 18 shows the effect of aconitine modification on the normalized steady-state inactivation curves of rNaV1.4 channels expressed in CHO cells. The channels were modified by perfusing the cells with buffered solution containing aconitine at the given concentrations and then simple pulses (10 ms pulses to 0 mV from −100 mV holding potential) were recorded until the currents leveled to a steady value (typically ~1000 pulses). Steady-state fast inactivation of the current was then determined by delivering 500 ms conditioning pulses to potentials ranging from −130 to −11 mV (7 my increments) immediately followed by a 10 ms test pulse to 0 mV to test the available current. The peak current measured during the test pulse was normalized to the maximum peak current recorded in the conditioning pulses. These data were fitted with a Boltzmann function ($1/(1+\exp(V-V_{0.5})/k)$) to determine $V_{0.5}$ and k values. The curves parameters of the fitted Boltzmann function are summarized in Table 4. Midpoint voltage $V_{0.5}$ represents the membrane potential at which half maximum current is observed; slope factor at midpoint k quantifies the rate at which the inactivation response occurs.

Figure 19:
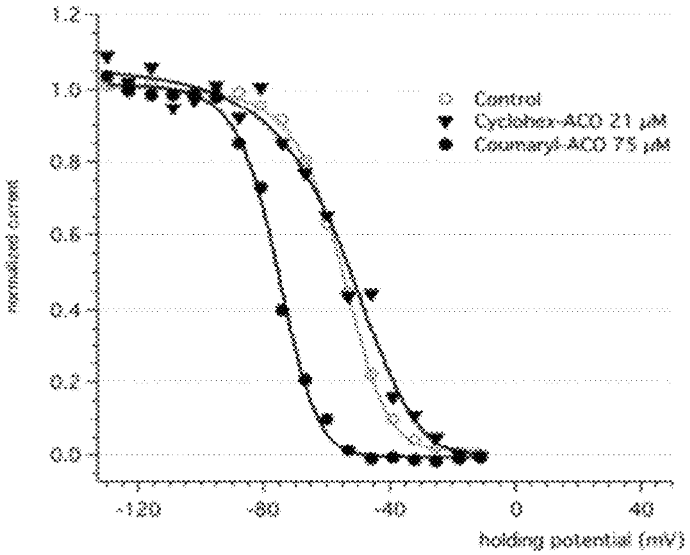
FIG. 19. Normalized steady-state inactivation of $Na_V$1.4 channels. Effect of selected compounds on the steady-state inactivation.

Aconitine modification elicited hyperpolarizing shifts in steady-state inactivation compared with the control data (labeled as "external" solution). The extent of this shift is concentration-dependent. The effect of varying the C14-ester of aconitine was examined and representative examples of the steady-state inactivation plots are shown in FIG. 19 (also summarized in Table 4). For instance, cyclohexanoate analog 4.8d restores the steady-state inactivation parameters back to the unmodified NaV (labeled "control", FIG. 19), while decreasing the slope factor k from ~6 to ~8 which indicates a slower inactivation response of the channel when bound to the molecule. In contrast, large aromatic ester substituents at C14 caused significant shifts toward hyperpolarized potentials. A representative example is the coumarinyl 4.8 g which shows 23 mV shift ($V_{0.5}$ of −76 mV) compared to the unmodified NaV channel ($V_{0.5}$ of −53 mV). Interestingly, these molecules impart steady-state inactivation shifts that mirror the effect of aconitine, however they do so at lower concentration.

TABLE 4

Summary of aconitine derivatives on the activation and inactivation properties.

| | | Activation | | Steady-state inactivation | |
|---|---|---|---|---|---|
| | | $V_{0.5}$ (mV) | $h_g$ | $V_{0.5}$ (mV) | k |
| Control rNav1.4 | — | −20.1 | 9.1 | −58.4 | 6.75 |
| Aconitine 5 μM | 1 | — | — | −65.1 | 6.50 |
| Aconitine 50 μM | 1 | −40.3 | 10.4 | −65 | 5.97 |
| Aconitine 200 μM | 1 | — | — | −82.4 | 21.0 |
| ACO-cyclohexanoate 21 μM | 4.8d | 1.3 | 15.4 | −53.1 | 8.1 |
| ACO-2'-naphthoate 5 μM | 4.8c | −23.1 | 13.1 | — | — |
| ACO-3'-acylcoumarin 75 μM | 4.8g | −36 | 8.9 | −75.6 | 11.6 |

Conclusions

C14-modified aconitine derivatatives have a unique effect on the properties of NaV channels. In the cases presented above, changing the benzoate moiety of aconitine for larger aromatic substitutents increased the hyperpolarizing shifts for the thresholds of both activation and steady-state inactivation. This demonstrates that lower concentrations of certain C14 analogs can be used to achieve the same physiological response as with aconitine.

Synthetic Materials and Methods

General. All reagents were obtained commercially unless otherwise noted. Reactions were performed using oven-dried glassware under an atmosphere of nitrogen. Air- and moisture sensitive liquids and solutions were transferred via syringe or stainless steel cannula. Organic solutions were concentrated under reduced pressure (ca. 15 Torr) by rotary evaporation. Tetrahydrofuran (THF) and acetonitrile (MeCN) and N,N-dimethylformamide were passed through two columns of activated alumina immediately prior to use. Chromatographic purification of products was accomplished using forced flow chromatography on Silicycle ultrapure silica gel (40-63 μm). Thin layer chromatography was performed on EM Science silica gel 60 $F_{254}$ plates (250 μm). Visualization of the developed chromatogram was accomplished by fluorescence quenching and by staining with aqueous ceric ammonium molybdate (CAM) solution.

Nuclear magnetic resonance (NMR) spectra were acquired on a Varian Mercury spectrometer operating at 400 and 100 MHz for $^1H$ and $^{13}C$, respectively, or on a Varian Inova spectrometer operating at 500 and 125 MHz for $^1H$ and $^{13}C$, respectively, and are referenced internally according to residual solvent signals. Data for $^1H$ NMR are recorded as follows: chemical shift (d, ppm), multiplicity (s, singlet; d, doublet; t, triplet; q, quartet; quint, quintet; m, multiplet; br, broad), integration, coupling constant (Hz). Data for $^{13}C$ NMR are reported in terms of chemical shift (d, ppm). High-resolution mass spectra were obtained from the Vincent Coates Foundation Mass Spectrometry Laboratory at Stanford University.

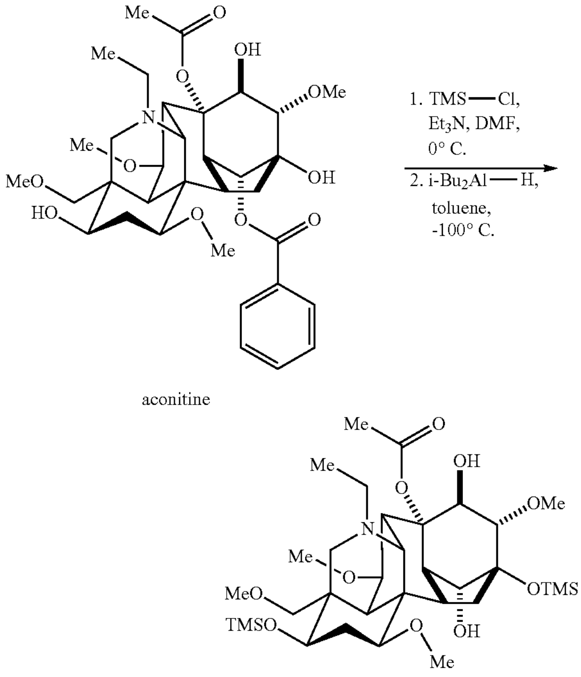

aconitine 4.6

4.6: To a solution of aconitine (100 mg, 0.16 mmol) in 3.9 mL of DMF at 0° C. was added $NEt_3$ (0.650 mL, 4.7 mmol, 30 equiv), followed by the dropwise addition of trimethylsilyl chloride (0.390 mL, 3.1 mmol, 20 equiv). The solution was stirred at 0° C. for 40 min, then poured into a separatory funnel containing 40 mL of a 1:1 mixture (v/v) of ethyl acetate/saturated aqueous $NaHCO_3$. The organic layer was removed, and the aqueous layer was extracted with 3×10 mL of ethyl acetate. The combined organic layers were washed with 20 mL of saturated aqueous NaCl, dried over $MgSO_4$, and concentrated under reduced pressure. The crude product was then concentrated from benzene three times to remove residual silane and water, affording 4.5 as a white solid, which was used without further purification.

A flask fitted with an internal thermometer was charged with a solution of 4.5 in 22 mL of toluene and the reaction was cooled to −100° C. A 1.0 M solution of diisobutylaluminum hydride in toluene (1.55 mL, 1.6 mmol, 10 equiv) was added dropwise, ensuring that the internal temperature did not exceed −95° C. Stirring was continued for 15 min, then the reaction was quenched by the addition of 2.5 mL of ethyl acetate, pre-cooled to −95° C., followed by 10 mL of saturated aqueous potassium sodium tartrate. The flask was then removed from the bath and allowed to warm to rt with vigorous stirring. The mixture was diluted with 10 mL of ethyl acetate and transferred to a separatory funnel. The layers were separated, and the aqueous layer was extracted with 3×10 mL of EtOAc. The combined organic layers were dried over $MgSO_4$ and concentrated. Chromatography on Davisil silica gel (gradient elution 5%→25% acetone/hexanes) provided 4.6 as a colorless oil (75.1 mg, 71% over two steps): TLC $R_f$=0.35 (1:1 hexanes/acetone); $^1$H NMR ($CDCl_3$, 500 MHz): δ 4.39-4.42 (m, 2H), 4.13 (d, 1H, J=6.8 Hz), 3.87 (d, 1H, J=5.1 Hz) 3.70 (dd, 1H, J=12.4, 5.2 Hz), 3.63 (d, 1H, J=7.9 Hz), 3.51 (s, 3H), 3.31 (d, 1H, J=8.2 Hz), 3.29 (s, 3H), 3.26 (s, 3H), 3.23 (s, 3H), 3.14 (d, 1H, J=4.2 Hz), 3.10 (s, 1H), 2.98 (dd, 1H, J=11.2, 6.4 Hz), 2.88 (s, 1H), 2.78 (d, 1H, J=11.1 Hz), 2.65-2.76 (m, 2H), 2.51 (d, 1H, J=4.6 Hz), 2.48 (d, 1H, J=12.4 Hz), 2.42 (d, 1H, J=1.8 Hz), 2.33-2.40 (m, 1H), 2.14 (d, 1H, J=6.6 Hz), 2.09 (s, 3H), 2.07-2.12 (m, 1H), 2.06 (d, 1H, J=10.1 Hz), 1.88-1.99 (m, 2H), 1.07 (t, 3H, J=7.1 Hz), 0.14 (s, 9H), 0.11 (s, 9H) ppm; IR (thin film): v 840, 1100, 1250, 1261, 1708, 2924, 2956, 3487 $cm^{-1}$; HRMS ($ES^+$) calcd for $C_{33}H_{58}N_1O_{10}Si_2$ 685.3678 found 686.3748 ($MH^+$).

A general two-step protocol was used to transform 4.6 into aconitine derivatives 4.8a-h. Experimental details for conversion of 4.6 to 4.8a are representative.

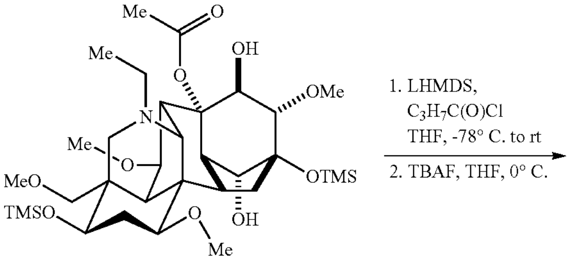

4.6

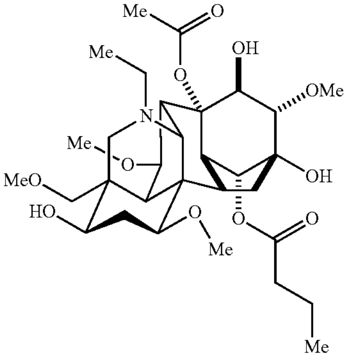

4.8a 4.8a: To a solution of 4.6 (10.0 mg, 0.015 mmol) in 1.2 mL of THF at −78° C. was added a solution of lithium bis(trimethylsilyl)amide (2.7 mg, 0.016 mmol, 1.1 equiv) in 0.6 mL of THF, and the reaction was stirred at −78° C. for 5 min. A solution of butyryl chloride (1.7 mg, 0.016 mmol, 1.1 equiv) in 0.3 mL of THF was then added, and the flask was removed from the bath and allowed to stir at rt for 1 hr. The reaction was quenched by the addition of 5 mL of saturated aqueous $NaHCO_3$, transferred to a separatory funnel, and extracted with 3×5 mL of ethyl acetate. The combined organic layers were washed with 5 mL of saturated aqueous NaCl, dried over $MgSO_4$, and concentrated.

Crude 4.7a was dissolved in 1.5 mL THF at 0° C. A 1 M solution of tetra-n-butylammonium fluoride in THF (44 μL, 0.044 mmol, 3 equiv) was added and the reaction was stirred at that 0° C. for 2 hrs. The reaction was quenched by addition of 5 mL of saturated aqueous $NH_4Cl$, then extracted with 3×5 mL of EtOAc. The combined organic layers were washed with 5 mL of saturated aqueous NaCl, dried over $MgSO_4$, filtered and concentrated under reduced pressure. Chromatography on silica (gradient elution 40%→50%→70%→100% THF/$CH_2Cl_2$) afforded 4.8a (5.1 mg, 57% over two steps) as a colorless film: TLC $R_f$=0.21 (1:1 THF/$CH_2Cl_2$); $^1$H NMR ($CDCl_3$, 500 MHz): δ 4.68 (d, 1H, J=5.0 Hz), 4.52 (d, 1H, J=2.6 Hz), 4.34 (dd, 1H, J=5.6, 2.6 Hz), 4.03 (d, 1H, J=6.7 Hz), 3.85 (s, 1H), 3.73-3.82 (m, 1H), 3.66 (s, 3H), 3.60 (d, 1H, J=8.8 Hz), 3.43 (d, 1H, J=8.8 Hz), 3.30 (s, 3H), 3.25 (s, 1H), 3.24 (s, 6H), 3.05-3.15 (m, 1H), 3.02 (s, 1H), 2.86 (d, 1H, J=10.7 Hz), 2.85 (s, 1H), 2.65-2.76 (m, 2H), 2.59 (d, 1H, J=10.6 Hz), 2.27-2.34 (m, 4H), 2.17-2.25 (m, 1H), 2.09-2.15 (m, 1H), 2.03-2.09 (m, 2H), 2.02 (s, 3H), 1.87-1.95 (m, 2H), 1.56-1.70 (m, 2H), 1.09 (t, 3H, J=7.0 Hz), 0.96 (t, 3H, J=7.4 Hz) ppm; IR (thin film): v 1098, 1185, 1269, 1712, 1737, 2929, 2967, 3486 $cm^{-1}$; HRMS ($ES^+$) calcd for $C_{31}H_{48}N_1O_{11}$ 611.3306 found 612.3376 ($MH^+$).

4.8b

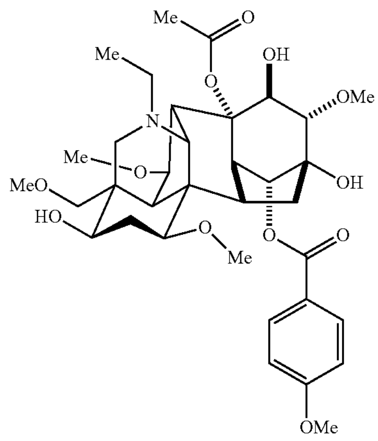

4.8b: TLC $R_f$=0.16 (1:1 THF/$CH_2Cl_2$); $^1$H NMR ($CDCl_3$, 500 MHz): δ 7.97 (d, 2H, J=9.0 Hz), 6.93 (d, 2H, J=9.0 Hz), 4.84 (d, 1H, J=5.1 Hz), 4.47 (dd, 1H, J=5.3, 1.9 Hz), 4.41 (d, 1H, J=2.3 Hz), 4.05 (d, 1H, J=6.3 Hz), 3.90-3.99 (br s, 1H), 3.87 (s, 3H), 3.81-3.87 (m, 1H), 3.75 (s, 3H), 3.61 (d, 1H, J=8.9 Hz), 3.49 (d, 1H, J=8.9 Hz), 3.32 (d, 1H, J=5.3 Hz), 3.30 (s, 3H), 3.27 (s, 3H), 3.17 (s, 3H), 3.09-3.17 (m, 2H), 2.94-3.05 (m, 1H), 2.86-2.92 (m, 1H), 2.84 (s, 1H), 2.74-2.83 (m, 1H), 2.56-2.65 (m, 1H), 2.31-2.54 (m, 4H), 2.10-2.22 (m, 3H), 1.88-1.94 (m, 1H), 1.44 (s, 3H), 1.14 (t, 3H, J=7.0 Hz) ppm (the NMR data of 4.8b matches that of jesaconitine previously identified via isolation: Keith et al., *J. Org. Chem.* 1968, 33, 2497-2499); IR (thin film): v 1099, 1259, 1280, 1606, 1712, 2926, 3489 $cm^{-1}$. (the IR spectra of 4.8b matches that of jesaconitine identified via isolation: Nakamura et al., *J. Nat. Med.* 2006, 60, 285-294) HRMS ($ES^+$) calcd for $C_{35}H_{48}N_1O_{12}$ 675.3255 found 676.3324 ($MH^+$).

4.8c

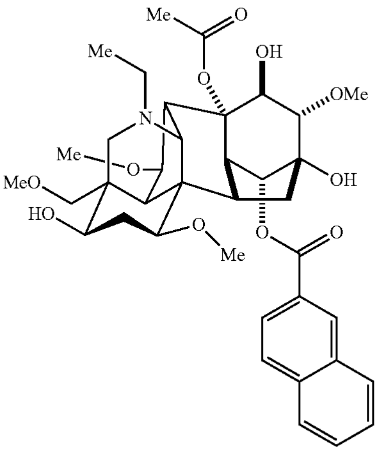

4.8c: TLC $R_f$=0.28 (1:1 THF/$CH_2Cl_2$); $^1H$ NMR ($CDCl_3$, 500 MHz): δ 8.61 (s, 1H), 8.03 (dd, 1H, 8.6, 1.6 Hz), 7.95 (dd, 1H, 8.1, 1.0 Hz), 7.91 (d, 1H, J=6.8 Hz), 7.89 (d, 1H, J=6.7 Hz), 7.62 (ddd, 1H, J=8.2, 7.0, 1.3 Hz), 7.57 (ddd, 1H, J=8.1, 6.9, 1.2 Hz), 4.93 (d, 1H, J=5.2 Hz), 4.55 (dd, 1H, J=5.4, 2.9 Hz), 4.41 (d, 1H, J=2.8 Hz), 4.06 (d, 1H, J=6.4 Hz), 4.02 (s, 1H), 3.81 (s, 3H), 3.75-3.80 (m, 1H), 3.63 (d, 1H, J=8.8 Hz), 3.50 (d, 1H, J=8.8 Hz), 3.38 (d, 1H, J=5.5 Hz), 3.30 (s, 3H), 3.29-3.32 (m, 1H), 3.28 (s, 3H), 3.16 (s, 3H), 3.10-3.15 (m, 2H), 2.93-2.97 (m, 1H), 2.90 (d, 1H, J=11.6 Hz), 2.85 (s, 1H), 2.70-2.79 (m, 2H), 2.31-2.41 (m, 3H), 2.09-2.20 (m, 3H), 1.96-2.04 (m, 1H), 1.33 (s, 3H), 1.11 (t, 3H, J=7.1 Hz) ppm; IR (thin film): ν 1102, 1284, 1712, 1721, 2921, 3346 $cm^{-1}$; HRMS ($ES^+$) calcd for $C_{38}H_{48}N_1O_{11}$ 695.3306 found 696.3375 ($MH^+$).

4.8d

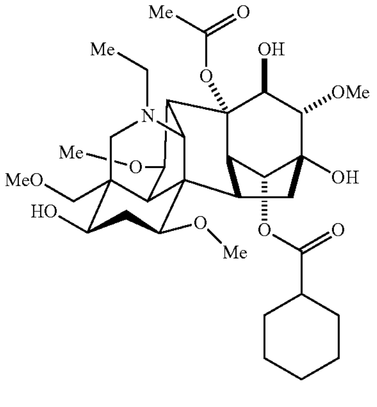

4.8d: TLC $R_f$=0.18 (1:1 THF/$CH_2Cl_2$); $^1H$ NMR ($CDCl_3$, 500 MHz): δ 4.68 (d, 1H, J=5.1 Hz), 4.56 (d, 1H, J=2.6 Hz), 4.35 (dd, 1H, J=5.4, 2.6 Hz), 4.03 (d, 1H, J=5.9 Hz), 3.85 (s, 1H), 3.74-3.81 (m, 1H), 3.66 (s, 3H), 3.59 (d, 1H, J=8.8 Hz), 3.42 (d, 1H, J=8.9 Hz), 3.30 (s, 3H), 3.24-3.26 (m, 1H), 3.24 (s, 3H), 3.23 (s, 3H), 3.07-3.14 (m, 1H), 3.01 (s, 1H), 2.86 (d, 1H, J=10.0 Hz), 2.85 (s, 1H), 2.65-2.76 (m, 2H), 2.57 (d, 1H, J=10.0 Hz), 2.30-2.43 (m, 3H), 2.19-2.29 (m, 1H), 2.13 (d, 1H, J=6.6 Hz), 2.02-2.10 (m, 2H), 2.02 (s, 3H), 1.86-1.94 (m, 3H), 1.72-1.78 (m, 2H), 1.62-1.68 (m, 1H), 1.32-1.42 (m, 2H), 1.17-1.31 (m, 4H), 1.09 (t, 3H, J=7.1 Hz) ppm; IR (thin film): ν 1094, 1268, 1709, 2929, 3469 $cm^{-1}$; HRMS ($ES^+$) calcd for $C_{34}H_{52}N_1O_n$ 651.3659 found 652.3690 ($MH^+$).

4.8e

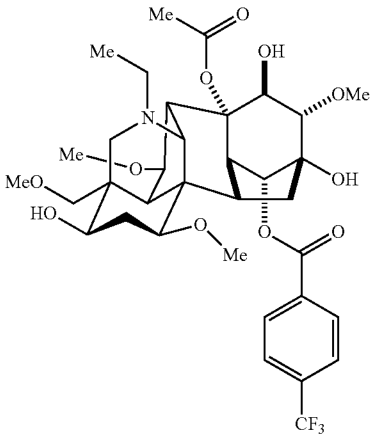

4.8e: TLC $R_f$=0.19 (1:1 THF/$CH_2Cl_2$); $^1H$ NMR ($CDCl_3$, 500 MHz): δ 8.15 (d, 2H, J=8.1 Hz), 7.75 (d, 2H, J=8.2 Hz), 4.89 (d, 1H, J=5.0 Hz), 4.43 (dd, 1H, J=5.4, 2.9 Hz), 4.40 (d, 1H, J=2.7 Hz), 4.04 (d, 1H, J=5.9 Hz), 3.95 (s, 1H), 3.75-3.82 (m, 1H), 3.75 (s, 3H), 3.63 (d, 1H, J=8.8 Hz), 3.49 (d, 1H, J=8.8 Hz), 3.34 (d, 1H, J=5.2 Hz), 3.27 (s, 3H), 3.30 (s, 3H), 3.18 (s, 3H), 3.09-3.17 (m, 2H), 2.87-2.91 (m, 2H), 2.85 (s, 1H), 2.67-2.78 (m, 2H), 2.30-2.45 (m, 4H), 2.07-2.19 (m, 3H), 1.95-2.03 (m, 1H), 1.44 (s, 3H), 1.06-1.15 (m, 3H) ppm; IR (thin film): ν 1100, 1282, 1325, 1720, 2930, 3502 $cm^{-1}$; HRMS ($ES^+$) calcd for $C_{35}H_{45}F_3N_1O_{11}$ 713.3023 found 714.3096 ($MH^+$).

4.8f

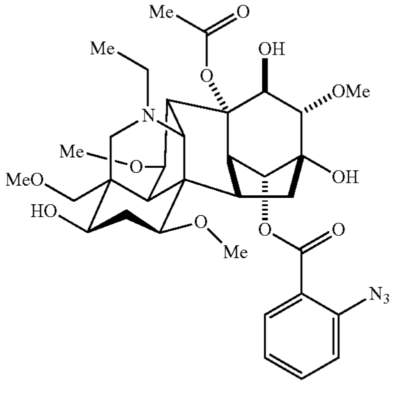

4.8f: TLC $R_f$=0.15 (1:1 THF/$CH_2Cl_2$); $^1H$ NMR ($CDCl_3$, 500 MHz): δ 7.95-7.94 (m, 1H), 7.58-7.55 (m, 1H), 7.23-7.20 (m, 1H), 4.85 (d, 1H, J=5.0 Hz), 4.52 (dd, 1H, J=5.5, 3.0 Hz), 4.20 (d, 1H, J=2.5 Hz), 4.06 (br d, 1H, J=6.0 Hz), 3.94 (s, 1H), 3.78 (dd, 1H, J=9.5, 4.5 Hz), 3.63 (d, 1H, J=9.0 Hz), 3.50 (d, 1H, J=8.5 Hz), 3.33 (d, 1H, J=4.0 Hz), 3.31 (s, 3H), 3.26 (s, 3H), 3.19 (s, 3H), 3.13 (dd, 1H, J=7.5, 5.5 Hz), 3.09 (s, 1H), 2.93-2.88 (m, 2H), 2.85 (s, 1H), 2.75-2.70 (m, 2H), 2.41-2.34 (m, 3H), 2.14-2.10 (m, 3H), 2.01-1.97 (ddd, 1H, J=12.5, 5.5, 5.5 Hz), 1.62 (s, 3H), 1.10 (t, 3H, J=7.0 Hz) ppm.

4.8g

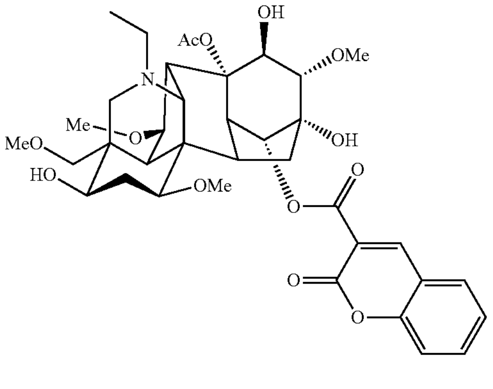

4.8 g: $^{1}$H NMR (500 MHz; $CDCl_3$): δ 8.58 (s, 1H), 7.72-7.69 (m, 1H), 7.64 (dd, J=8.0, 1.4 Hz, 1H), 7.43-7.36 (m, 2H), 4.94 (d, J=4.9 Hz, 1H), 4.70 (dd, J=5.3, 2.9 Hz, 1H), 4.53 (d, J=2.8 Hz, 1H), 4.08 (d, J=6.2 Hz, 1H), 4.01 (s, 1H), 3.81 (dd, J=9.0, 4.8 Hz, 2H), 3.73 (s, 3H), 3.66 (d, J=8.9 Hz, 1H), 3.50 (d, J=8.9 Hz, 1H), 3.37 (d, J=8.9 Hz, 1H), 3.33 (s, 3H), 3.28 (s, 3H), 3.24 (s, 3H), 3.15 (t, J=6.6 Hz, 1H), 3.11 (s, 1H), 2.98-2.84 (m, 3H), 2.82-2.68 (m, 2H), 2.51-2.34 (m, 3H), 2.25-2.11 (m, 3H), 2.06-1.96 (m, 1H), 1.90 (s, 3H), 1.12 (t, J=7.1 Hz, 3H). $^{13}$C NMR ($CDCl_3$, 125 MHz): a 172.8, 162.7, 156.6, 155.5, 149.8, 135.1, 130.0, 125.3, 118.0, 117.7, 117.2, 92.1, 89.8, 83.7, 82.6, 79.9, 77.9, 74.4, 71.8, 61.1, 60.9, 59.4, 58.4, 56.2, 50.3, 49.2, 47.3, 46.7, 44.9, 44.6, 43.3, 41.1, 36.0, 33.7, 22.5, 13.6 ppm. IR (thin film): 3490 (br.), 2969, 2926, 2821, 1755, 1710, 1610, 1566, 1454, 1371, 1269, 1240, 1211, 1097, 761 $cm^{-1}$. HRMS ($ES^+$) calcd for $C_{37}H_{48}O_{13}N$=714.3120. found 714.3121 [$MH^+$].

4.8h

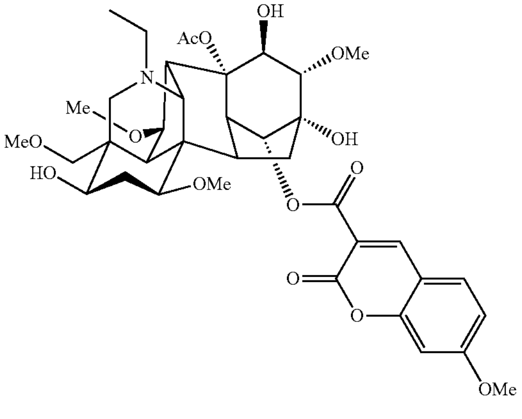

4.8h: $^{1}$H NMR (400 MHz; $CDCl_3$): δ 8.51 (s, 1H), 7.50 (d, J=8.8 Hz, 1H), 6.92 (dd, J=8.6, 2.4 Hz, 1H), 6.81 (d, J=2.3 Hz, 1H), 4.94-4.86 (m, 1H), 4.72-4.64 (m, 1H), 4.49 (d, J=2.3 Hz, 1H), 4.06 (d, J=5.6 Hz, 1H), 3.97 (s, 1H), 3.92 (s, 3H), 3.81-3.75 (m, 2H), 3.71 (s, 3H), 3.67-3.61 (m, 1H), 3.52-3.47 (m, 1H), 3.35-3.32 (m, 1H), 3.31 (s, 3H), 3.26 (s, 3H), 3.22 (s, 3H), 3.14-3.06 (m, 2H), 2.91-2.82 (m, 3H), 2.46-2.27 (m, 2H), 2.17-2.04 (m, 3H), 2.01-1.96 (m, 1H), 1.86 (s, 3H), 1.13-1.03 (m, 3H) ppm. $^{13}$C NMR ($CDCl_3$, 125 MHz): a 172.8, 165.8, 163.0, 158.0, 157.0, 150.0, 139.5, 131.2, 114.1, 113.4, 111.7, 100.6, 92.1, 89.9, 83.7, 82.7, 79.6, 74.4, 71.9, 61.3, 61.0, 59.4, 58.4, 56.3, 56.2, 50.1, 49.1, 47.1, 44.9, 43.3, 40.7, 36.0, 33.4, 31.0, 30.0, 29.6, 22.5, 13.6 ppm. IR (thin film): 3486 (br.), 3077, 2925, 2853, 1762, 1748, 1711, 1609, 1558, 1506, 1462, 1376, 1265, 1212, 1102, 1026, 915, 732 $cm^{-1}$. HRMS ($ES^+$) calcd for $C_{38}H_{50}O_{14}N$=744.3226. found 744.3229 [$MH^+$].

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A compound represented by structural formula (II):

(II)

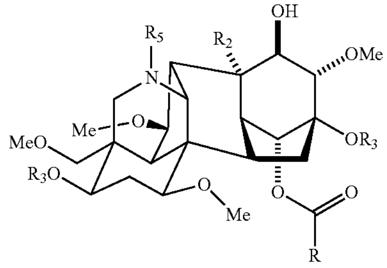

or a pharmaceutically acceptable salt thereof, wherein:

R is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalky, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

$R_2$ is alkyl, alkoxy, or,

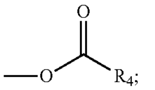

each $R_3$ is independently hydrogen or a silyl protecting group;

each $R_4$ is alkyl, alkenyl, alkynyl, alkoxy, alkylamino, aryl, aryloxy, arylamino, aralkoxy, aralkamino, heteroaryl, heteroaryloxy, heteroarylamino, heteroaralkyl, heteroaralkoxy, heteroaralkamino, cycloalky, cycloalkenyl, cycloalkoxy, cycloalkamino, heterocyclyl, heterocyclyloxy, heterocyclylamino, heterocyclylalky, heterocyclylalkoxy, or heterocyclylalkamino, and is optionally substituted with 1 to 3 A groups;

each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sufonyl, sulfonamindo, or azido; and $R_5$ is alkyl;

provided that, when R is unsubstituted phenyl, $R_2$ is

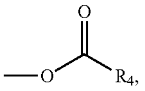

and each $R_3$ is hydrogen, then $R_4$ is not alkyl or alkenyl; and when R is p-methoxyphenyl, $R_2$ is

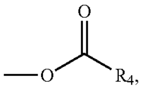

and each $R_3$ is hydrogen, then $R_4$ is not methyl.

2. The compound of claim 1, wherein each $R_3$ is hydrogen.

3. The compound of claim 1, wherein $R_2$ is

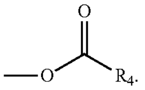

4. The compound of claim 3, wherein $R_4$ is alkyl.

5. The compound of claim 4, wherein $R_4$ is methyl.

6. The compound of claim 1, wherein $R_5$ is methyl or ethyl.

7. The compound of claim 6, wherein $R_5$ is ethyl.

8. The compound of claim 1, wherein R is alkyl, aryl, heteroaryl, heterocyclyl, or cycloalkyl, and is optionally substituted with 1 to 3 A groups.

9. The compound of claim 8, wherein R is alkyl, phenyl, naphthyl, cyclohexyl, or coumarinyl, and is optionally substituted with 1 to 3 A groups.

10. The compound of claim 9, wherein the A groups are independently alkyl, alkoxyl, halo, trihalomethyl, or azido.

11. The compound of claim 8, wherein R is aryl, heteroaryl, or cycloalkyl, and is optionally substituted with 1 to 3 A groups.

12. The compound of claim 1, wherein R is selected from any one of the following:

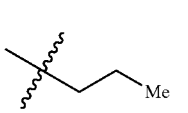
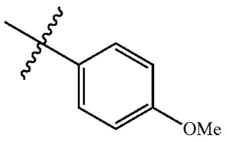
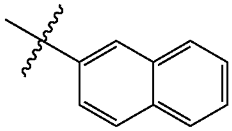
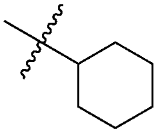

-continued

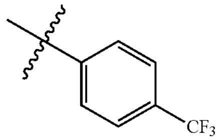
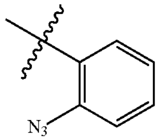
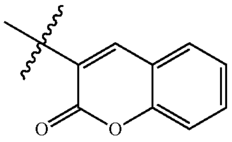
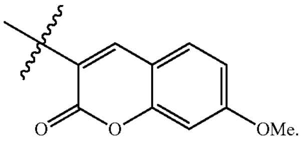

13. The compound of claim 12, wherein R is

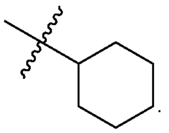 [SMILES: *C1CCCCC1]

14. The compound of claim 1, wherein each $R_3$ is a silyl protecting group.

15. The compound of claim 1, wherein the protecting group is t-butyldimethylsilyl or trimethylsilyl.

16. The compound of claim 15, wherein the protecting group is trimethylsilyl.

17. The compound of claim 1, wherein the compound modulates the activity of voltage-gated sodium channel 1.4.

18. The compound of claim 17, wherein the compound causes the sodium channel to open.

19. The compound of claim 18, wherein the compound causes the sodium channel to open at a lower membrane potential than aconitine.

20. The compound of claim 17, wherein the compound causes decreased flow of sodium through the sodium channel.

21. A pharmaceutical composition comprising the compound of claim 1 and a pharmaceutically acceptable carrier.

22. A packaged pharmaceutical comprising the pharmaceutical composition of claim 21 and instructions for using the composition to treat pain in a mammalian subject.

23. A method of treatment in a subject, comprising administering to the subject a compound of claim 1 in an amount effective to treat the subject, wherein the subject suffers from pain.

24. The method of claim 23, wherein the treatment modulates neuronal activity in the subject.

25. The method of claim 23, wherein the pain is acute pain, anal fissure pain, arthritis pain, back pain, blepharospasm pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, or pain from dysmenorrhea.

26. A method of preparing the aconitine derivative of claim 1, comprising the step of:

i) selectively protecting an aconitine congener at the C-3 and C-13 hydroxyl groups.

27. The method of claim 26, wherein the selective protection is with a silyl group.

28. The method of claim 27, wherein the silyl group is a t-butyldimethylsilyl group or a trimethylsilyl group.

29. The method of claim 28, wherein the silyl group is a trimethylsilyl group.

30. The method of claim 26, further comprising the step of selectively cleaving the C-14 ester of the protected aconitine congener.

31. The method of claim 30, wherein the selective cleavage is a reductive cleavage.

32. The method of claim 31, wherein the reductive cleavage is by diisobutylaluminum hydride.

33. The method of claim 30, further comprising the step of selectively modifying the C-14 hydroxyl group of the cleaved protected aconitine congener.

34. The method of claim 33, wherein the selective modification is an acylation.

35. The method of claim 26, wherein the aconitine congener is aconitine or mesaconitine.

36. The method of claim 35, wherein the aconitine congener is aconitine.

* * * * *